United States Patent
Messmer

(10) Patent No.: US 8,354,106 B2
(45) Date of Patent: Jan. 15, 2013

(54) ANTIBODIES AGAINST HMGB1 AND FRAGMENTS THEREOF

(75) Inventor: Davorka Messmer, La Jolla, CA (US)

(73) Assignee: The Feinstein Institute for Medical Research, Manhasset, NY (US)

( * ) Notice: Subject to any disclaimer, the term of this patent is extended or adjusted under 35 U.S.C. 154(b) by 1347 days.

(21) Appl. No.: 11/922,259

(22) PCT Filed: Jun. 15, 2006

(86) PCT No.: PCT/US2006/023255
§ 371 (c)(1),
(2), (4) Date: Feb. 5, 2008

(87) PCT Pub. No.: WO2006/138429
PCT Pub. Date: Dec. 28, 2006

(65) Prior Publication Data
US 2011/0268738 A1 Nov. 3, 2011

Related U.S. Application Data

(60) Provisional application No. 60/690,983, filed on Jun. 16, 2005.

(51) Int. Cl.
A61K 39/395 (2006.01)
(52) U.S. Cl. .................. 424/145.1; 530/388.23
(58) Field of Classification Search .......... None
See application file for complete search history.

(56) References Cited

FOREIGN PATENT DOCUMENTS

| WO | WO 2004044001 A2 * | 5/2004 |
|---|---|---|
| WO | WO 2004/046345 A2 | 6/2004 |
| WO | WO 2005/026209 A2 | 3/2005 |
| WO | WO 2006/083301 A2 | 8/2006 |

OTHER PUBLICATIONS

Bonaldi et al., The EMBO Journal vol. 22 No. 20 pp. 5551-5560.*
Paitier-Tonneau et al., Leucocyte Typing VI, "CD4 workshop panel report", Kishimoto et al. eds., Garland Publishing, Inc., 1998, pp. 49-54.*
Shore et al., J. Mol. Biol. (2006) 358, 347-354.*
Mylvaganam et al., J. Mol. Biol. (1998) 281, 301-322.*
Engstrom et al., Journal of Immunological Methods 297 (2005) 203-211.*
Nap et al., Cancer Research, 52, pp. 2329-2339, Apr. 15. 1992.*
Schnell et al., Eur J Biochem 200,487-493 (1991).*
Li, J., et al., "Structural Basis for the Proinflammatory Cytokine Activity of High Mobility Group Box 1," Molecular Medicine 9(1-2):37-45 (2003).
Messmer, D., et al., "High Mobility Group Box Protein 1: An Endogenous Signal for Dendritic Cell Maturation and Th1 Polarization," J. Immunology 173:307-313 (2004).
Communication pursuant to Article 94(3) EPC, EP 06 784 906.7 dated Jul. 22, 2011.
European Search Report for EP Application No. 11001066.7, 7 pages, dated Jul. 13, 2011.
Communication pursuant to Article 94(3) EPC, Application No. 06 784 906.7, dated Feb. 10, 2009.
Communication pursuant to Article 94(3) EPC—06 784 906.7 dated Sep. 27, 2010.
Notification Concerning Transmittal of International Preliminary Report on Patentability (IPER) with IPER and Written Opinion, Application No. PCT/US2006/023255, mailed Jan. 3, 2008.
Notification of Transmittal of the International Search Report (ISR) and the Written Opinion (WO) of the International Searching Authority, or the Declaration, with ISR and WO., Application No. PCT/US2006/023255, mailed Mar. 13, 2007.
Abraham, E., et al., "Cutting Edge: HMG-1 as a Mediator of Acute Lung Inflammation," The Journal of Immunology 165:2950-2954 (2000).
Andersson, U. and Erlandsson-Harris, H., "HMGB1 is a Potent Trigger of Arthritis," Journal of Internal Medicine 255:344-350 (2004).
Kokkola, R., et al., "Successful Treatment of Collagen-Induced Arthritis in Mice and Rats by Targeting Extracellular High Mobility Group Box Chromosomal Protein 1 Activity," Arthritis & Rheumatism 48(7):2052-2058 (2003).
Telusma, G., et al., "Dendritic Cell Activating Peptides Induce Distinct Cytokine Profiles," International Immunology 18(11):1563-1573 (2006).
Wang, H., et al., "Extracellular Role of HMGB1 in Inflammation and Sepsis," Journal of Internal Medicine 255:320-331 (2004).
Wang, H., "HMG-1 as a Late Mediator of Endotoxin Lethality in Mice," Science 285:248-250 (1999).

* cited by examiner

Primary Examiner — Zachary Skelding
(74) Attorney, Agent, or Firm — Hamilton, Brook, Smith & Reynolds, PC

(57) ABSTRACT

In various embodiments, the present invention is drawn to antibodies or antigen-binding fragments thereof that bind to particular fragments of HMGB1, methods of treating a condition in a subject characterized by activation of an inflammatory cytokine cascade, methods of detecting and/or identifying an agent that binds to an HMGB1 polypeptide or fragment thereof, and methods of detecting HMGB1 in a sample.

11 Claims, 5 Drawing Sheets

CD86

MHC-II

CD40

HMGB1 mgkgdpkkpr gkmssyaffv qtcreehkkk hpdasvnfse fskkcserwk tmsakekgkf
edmakadkar yeremktyip pkgetkkkfk dpnapkrpps afflfcseyr pkikgehpgl
sigdvakklg emwnntaadd kqpyekkaak lkekyekdia ayrakgkpda akkgvvkaek
skkkkeeeed eedeedeeee edeededeee dddde (SEQ ID NO:1)

FIG. 5A

HMGB1 A Box:

pr gkmssyaffv qtcreehkkk hpdasvnfse fskkcserwk tmsakekgkf
edmakadkar yeremktyip pkget (SEQ ID NO:2)

FIG. 5B

HMGB1 B Box:

fk dpnapkrpps afflfcseyr pkikgehpgl sigdvakklg emwnntaadd
kqpyekkaak lkekyekdia ay (SEQ ID NO:3)

FIG. 5C

ANTIBODIES AGAINST HMGB1 AND FRAGMENTS THEREOF

RELATED APPLICATIONS

This application is the U.S. National Stage of International Application No. PCT/US2006/023255, filed Jun. 15, 2006, published in English, which claims the benefit of U.S. Provisional Application No. 60/690,983, filed Jun. 16, 2005.

The entire teachings of the above applications are incorporated herein by reference.

BACKGROUND OF THE INVENTION

Inflammation is often induced by proinflammatory cytokines, such as tumor necrosis factor (TNF), interleukin (IL)-1α, IL-1β, IL-6, macrophage migration inhibitory factor (MIF), and other compounds. These proinflammatory cytokines are produced by several different cell types, most importantly immune cells (for example, monocytes, macrophages and neutrophils), but also non-immune cells such as fibroblasts, osteoblasts, smooth muscle cells, epithelial cells, and neurons. These proinflammatory cytokines contribute to various disorders during the early stages of an inflammatory cytokine cascade.

The early proinflammatory cytokines (e.g., TNF, IL-1, etc.) mediate inflammation, and induce the late release of high mobility group box 1 (HMGB1; also known as HMG-1 and HMG1), a protein that accumulates in serum and mediates delayed lethality and further induction of early proinflammatory cytokines. HMGB1 was first identified as the founding member of a family of DNA-binding proteins, termed high mobility group box (HMGB) proteins, which are critical for DNA structure and stability. It was identified as a ubiquitously-expressed nuclear protein that binds double-stranded DNA without sequence specificity. The HMGB1 molecule has three domains: two DNA binding motifs termed HMGB A and HMGB B boxes, and an acidic carboxyl terminus. The two HMGB boxes are highly conserved 80 amino acid, L-shaped domains. HMG boxes are also expressed in other transcription factors including the RNA polymerase I transcription factor human upstream-binding factor and lymphoid-specific factor.

HMGB1 has been implicated as a cytokine mediator of delayed lethality in endotoxemia (Andersson, U., et al., *J. Exp. Med.* 192(4):565-570 (2000)). That work demonstrated that bacterial endotoxin (lipopolysaccharide (LPS)) activates monocytes/macrophages to release HMGB1 as a late response to activation, resulting in elevated serum HMGB1 levels that are toxic. Antibodies against HMGB1 prevent lethality from endotoxin even when antibody administration is delayed until after the early cytokine response. Like other proinflammatory cytokines, HMGB1 is a potent activator of monocytes. It has been demonstrated that intratracheal application of HMGB1 causes acute lung injury, and anti-HMGB1 antibodies protect against endotoxin-induced lung edema (Abraham, E., et al., *J. Immunol.* 165:2950-2954 (2000)). It has further been shown that serum HMGB1 levels are elevated in critically ill patients with sepsis or hemorrhagic shock, and levels are significantly higher in non-survivors as compared to survivors (U.S. Pat. No. 6,303,321). In vivo administration of HMGB1 has been shown to induce arthritis when injected into murine joints (Pullerits, R., et al., *Arthritis Rheum.* 481693-1700 (2003)).

HMGB1 has also been implicated as a ligand for RAGE, a multi-ligand receptor of the immunoglobulin superfamily. RAGE is expressed on endothelial cells, smooth muscle cells, monocytes, and nerves, and ligand interaction transduces signals through MAP kinase, P21 ras, and NF-κB. In addition, HMGB1 binds Toll-like receptor 2 (TLR2) and inhibition of this interaction can decrease or prevent inflammation (U.S. Published Application No. 20040053841). It has also been shown that receptor signal transduction of HMGB1 occurs in part through Toll-like receptor 4 (TLR4) (Park, J. S. et al., *J. Biol. Chem.* 279(9):7370-77 (2004)).

The delayed kinetics of HMGB1 appearance during endotoxema make it a potentially good therapeutic target, but little is known about the molecular basis of HMGB1 signaling and toxicity. Given the importance of HMGB1 in mediating inflammation, it would be useful to identify antibodies that bind HMGB1 and fragments thereof, for diagnostic and therapeutic purposes.

SUMMARY OF THE INVENTION

In various embodiments, the present invention is an antibody or antigen-binding fragment thereof that binds to a particular fragment of HMGB1, a method of treating a condition in a subject characterized by activation of an inflammatory cytokine cascade, a method of detecting and/or identifying an agent that binds to a particular fragment of HMGB1, and a method of detecting an HMGB1 polypeptide or fragment thereof in a sample.

In one embodiment, the invention is an antibody or antigen-binding fragment thereof that specifically binds to a fragment of HMGB1, wherein the fragment of HMGB1 is selected from the group consisting of Hp-16 (YAFFVQTCREEHKKKHPD; SEQ ID NO:5), Hp-31 (HPDASVNFSEFSKKKCSER; SEQ ID NO:6), Hp-91 (DPNAPKRPPSAFFLFCSE; SEQ ID NO:10) and Hp-106 (CSEYRPKIKGEBPGLSIG; SEQ ID NO:11).

In another embodiment, the invention is an antibody or antigen-binding fragment thereof that specifically binds to a fragment of HMGB1, wherein the fragment of HMGB1 is selected from the group consisting of Hp-16 (SEQ ID NO:5), Hp-31 (SEQ ID NO:6) and Hp-91 (SEQ ID NO:10).

In a particular embodiment, the invention is an antibody or antigen-binding fragment thereof that specifically binds to Hp-16 (YAFFVQTCREEHKKKHPD; SEQ ID NO:5).

In another embodiment, the invention is an antibody or antigen-binding fragment thereof that specifically binds to Hp-31 (HPDASVNFSEFSKKKCSER; SEQ ID NO:6).

In yet another embodiment, the invention is an antibody or antigen-binding fragment thereof that specifically binds to Hp-91 (DPNAPKRPPSAFFLFCSE; SEQ ID NO:10).

In still another embodiment, the invention is an antibody or antigen-binding fragment thereof that specifically binds to Hp-106 (CSEYRPKIKGEHPGLSIG; SEQ ID NO:11).

In one embodiment, the invention is an antibody or antigen-binding fragment thereof that specifically binds to an epitope of HMGB1 comprising amino acid residues 106-108 of HMGB1 (Cys-Ser-Glu).

In particular embodiments, the antibody or antigen-binding fragment of the invention inhibits release of a cytokine (e.g., IL-6, IL-12, TNF-α, IL-18, IL-8, IL-2, IL-1β and/or IL-5) from a vertebrate cell treated with HMGB1. In other embodiments, the antibody or antigen-binding fragment is an antigen-binding fragment (e.g., an Fab fragment, an Fab' fragment, an F(ab')$_2$ fragment, an Fv fragment). In yet other embodiments, the antibody or antigen-binding fragment is a monoclonal antibody or an antigen-binding fragment thereof. In still other embodiments, the antibody or antigen-binding fragment is a human antibody, a humanized antibody, a chimeric antibody, or an antigen-binding fragment of any of the foregoing.

In one embodiment, the invention is an isolated cell that produces an antibody or antigen-binding fragment thereof that specifically binds to a fragment of HMGB1, wherein said fragment of HMGB1 is selected from the group consisting of Hp-16 (SEQ ID NO:5), Hp-31 (SEQ ID NO:6), Hp-91 (SEQ ID NO:10) and Hp-106 (SEQ ID NO:11).

In another embodiment, the invention is a composition comprising an antibody or antigen-binding fragment of the invention and a pharmaceutically-acceptable excipient.

In one embodiment, the invention is a method of treating a condition in a subject characterized by activation of an inflammatory cytokine cascade comprising administering to the subject a therapeutically effective amount of an antibody or antigen-binding fragment of the invention. In one embodiment, the antibody or antigen-binding fragment that is administered to the subject specifically binds to Hp-16 (SEQ ID NO:5). In another embodiment, the antibody or antigen-binding fragment that is administered to the subject specifically binds to Hp-31 (SEQ ID NO:6). In yet another embodiment, the antibody or antigen-binding fragment that is administered to the subject specifically binds to Hp-91 (SEQ ID NO:10). In still another embodiment, the antibody or antigen-binding fragment that is administered to the subject specifically binds to Hp-106 (SEQ ID NO:11). In one embodiment, the condition to be treated is sepsis, allograft rejection, arthritis, asthma, lupus, adult respiratory distress syndrome, chronic obstructive pulmonary disease, psoriasis, pancreatitis, peritonitis, burns, ischemia, Behcet's disease, graft versus host disease, inflammatory bowel disease, multiple sclerosis and/or cachexia. In other embodiments, the condition is sepsis, arthritis or lupus.

In one embodiment, the invention is a method of detecting and/or identifying an agent that binds to HMGB1 or a fragment thereof and inhibits release of a cytokine from a vertebrate cell treated with HMGB1. In the method, an antibody or antigen-binding fragment of the invention, a test agent, and a composition comprising an HMGB1 polypeptide or a fragment thereof are combined, and the formation of a complex between the antibody or antigen-binding fragment and the HMGB1 polypeptide or fragment thereof is detected or measured. A decrease in formation of complex between the antibody or antigen-binding fragment and HMGB1 or fragment thereof, as compared to a suitable control, indicates that the test agent binds to the HMGB1 polypeptide or fragment thereof.

In one embodiment, the invention is a method of detecting an HMGB1 polypeptide or fragment thereof in a sample. In the method, a sample is contacted with an antibody or antigen-binding fragment of the invention, under conditions suitable for binding of the antibody or antigen-binding fragment to an HMGB1 polypeptide or fragment thereof present in the sample. If antibody-HMGB1 polypeptide complexes, antigen-binding fragment-HMGB1 polypeptide complexes, antibody-HMGB1 fragment complexes or antigen-binding fragment-HMGB1 fragment complexes are detected, their presence is indicative of an HMGB1 polypeptide or fragment thereof in the sample.

In one embodiment, the invention is a test kit for use in detecting the presence of an HMGB1 polypeptide or fragment thereof in a sample. In this embodiment, the test kit comprises an antibody or antigen-binding fragment of the invention and one or more ancillary reagents suitable for detecting the presence of a complex between the antibody or antigen-binding fragment and an HMGB1 polypeptide or fragment thereof.

BRIEF DESCRIPTION OF THE DRAWINGS

FIG. 5A is the amino acid sequence of a human (*Homo sapiens*) HMGB1 polypeptide (SEQ ID NO:1).

FIG. 5B is an A box of a human (*Homo sapiens*) HMGB1 polypeptide (SEQ ID NO:2).

FIG. 5C is a B box of a human (*Homo sapiens*) HMGB1 polypeptide (SEQ ID NO:3).

DETAILED DESCRIPTION OF THE INVENTION

Figure 1A:
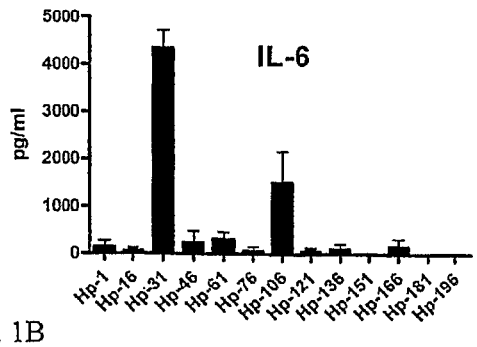
FIG. 1A is a bar graph depicting the quantity of the cytokine, IL-6, which is secreted by human immature monocyte-derived dendritic cells (DCs) following stimulation with various HMGB1-derived peptides that span the HMGB1 protein. Results represent the mean+/− standard error of the mean (SEM) of two independent experiments, which were conducted using DCs that were generated from different donors.

In various embodiments, the present invention is an antibody or antigen-binding fragment thereof that specifically binds to HMGB1, a method of treating a condition in a subject characterized by activation of an inflammatory cytokine cascade, a method of detecting and/or identifying an agent that binds to HMGB1 or a fragment thereof, and a method of detecting HMGB1 or a fragment thereof in a sample. In particular, the invention is drawn to antibodies or antigen-binding fragments that bind to specific fragments of HMGB1 and methods that utilize such antibodies and antigen-binding fragments.

Antibodies and Antibody Producing Cells

In one embodiment, the present invention encompasses antibodies or antigen-binding fragments thereof that bind to a fragment of HMGB1, wherein the fragment of HMGB1 is selected from the group consisting of Hp-16 (YAFFVQT-CREEHKKKHPD; SEQ ID NO:5), Hp-31 (HPDASVNF-SEFSKKCSER; SEQ ID NO:6), Hp-91 (DPNAPKRPPSAF-FLFCSE; SEQ ID NO:10) and Hp-106 (CSEYRPKIKGEHPGLSIG; SEQ ID NO:11). In a particular embodiment, the invention is an antibody or antigen-binding fragment thereof that specifically binds to Hp-16 (SEQ ID NO:5). In another embodiment, the invention is an antibody or antigen-binding fragment thereof that specifically binds to Hp-31 (SEQ ID NO:6). In yet another embodiment, the invention is an antibody or antigen-binding fragment thereof that specifically binds to Hp-91 (SEQ ID NO:10). In still another embodiment, the invention is an antibody or antigen-binding fragment thereof that specifically binds to Hp-106 (SEQ ID NO:11). As demonstrated herein, particular fragments of HMGB1 (e.g., Hp-16, Hp-31, Hp-91 and Hp-106) induce secretion of cytokines (e.g., proinflammatory cytokines) and chemokines. In addition, such fragments of HMGB1 also induce phenotypic and functional maturation of dendritic cells.

The antibodies of the invention can be polyclonal or monoclonal, and the term "antibody" is intended to encompass both polyclonal and monoclonal antibodies. The terms polyclonal and monoclonal refer to the degree of homogeneity of an antibody preparation, and are not intended to be limited to particular methods of production. In one embodiment, the antibody or antigen-binding fragment is a monoclonal antibody or antigen-binding fragment thereof. The term "monoclonal antibody" or "monoclonal antibody composition", as used herein, refers to a population of antibody molecules that contain only one species of an antigen binding site capable of immunoreacting with a particular epitope of a polypeptide of the invention. A monoclonal antibody composition thus typically displays a single binding affinity for a particular polypeptide of the invention with which it immunoreacts.

The term "antibody" as used herein also encompasses functional fragments of antibodies, including fragments of chimeric, humanized, primatized, veneered or single chain antibodies. Functional fragments include antigen-binding fragments of antibodies that bind to HMGB1 (e.g., a mammalian (e.g., human) HMGB1 polypeptide). For example, antibody fragments capable of binding to an HMGB1 polypeptide or a fragment thereof, include, but are not limited to Fv, Fab, Fab' and F(ab')$_2$ fragments. Such fragments can be produced by enzymatic cleavage or by recombinant techniques. For example, papain or pepsin cleavage can generate Fab or F(ab')$_2$ fragments, respectively. Other proteases with the requisite substrate specificity can also be used to generate Fab or F(ab')$_2$ fragments. Antibodies can also be produced in a variety of truncated forms using antibody genes in which one or more stop codons have been introduced upstream of the natural stop site. For example, a chimeric gene encoding a F(ab')$_2$ heavy chain portion can be designed to include DNA sequences encoding the CH$_1$ domain and hinge region of the heavy chain.

Single chain antibodies, and chimeric, humanized or primatized (CDR-grafted), or veneered antibodies, as well as chimeric, CDR-grafted or veneered single chain antibodies, comprising portions derived from different species, and the like are also encompassed by the present invention and the term "antibody". The various portions of these antibodies can be joined together chemically by conventional techniques, or can be prepared as a contiguous protein using genetic engineering techniques. For example, nucleic acids encoding a chimeric or humanized chain can be expressed to produce a contiguous protein. See, e.g., Cabilly et al., U.S. Pat. No. 4,816,567; Cabilly et al., European Patent No. 0,125,023 B1; Boss et al., U.S. Pat. No. 4,816,397; Boss et al, European Patent No. 0,120,694 B1; Neuberger, M. S. et al., WO 86/01533; Neuberger, M. S. et al., European Patent No. 0,194,276 B1; Winter, U.S. Pat. No. 5,225,539; Winter, European Patent No. 0,239,400 B1; Queen et al., European Patent No. 0 451 216 B1; and Padlan, E. A. et al., EP 0 519 596 A1. See also, Newman, R. et al., *BioTechnology*, 10: 1455-1460 (1992), regarding primatized antibody, and Ladner et al., U.S. Pat. No. 4,946,778 and Bird, R. E. et al., *Science*, 242: 423-426 (1988)) regarding single chain antibodies.

Humanized antibodies can be produced using synthetic or recombinant DNA technology using standard methods or other suitable techniques. Nucleic acid (e.g., cDNA) sequences coding for humanized variable regions can also be constructed using PCR mutagenesis methods to alter DNA sequences encoding a human or humanized chain, such as a DNA template from a previously humanized variable region (see e.g., Kamman, M., et al., *Nucl. Acids Res.*, 17: 5404 (1989)); Sato, K., et al., *Cancer Research*, 53: 851-856 (1993); Daugherty, B. L. et al., *Nucleic Acids Res.*, 19(9): 2471-2476 (1991); and Lewis, A. P. and J. S. Crowe, *Gene*, 101: 297-302 (1991)). Using these or other suitable methods, variants can also be readily produced. In one embodiment, cloned variable regions can be mutated, and sequences encoding variants with the desired specificity can be selected (e.g., from a phage library; see e.g., Krebber et al., U.S. Pat. No. 5,514,548; Hoogenboom et al., WO 93/06213).

The antibody can be a humanized antibody comprising one or more immunoglobulin chains (e.g., an antibody comprising a CDR of nonhuman origin (e.g., one or more CDRs derived from an antibody of nonhuman origin) and a framework region derived from a light and/or heavy chain of human origin (e.g., CDR-grafted antibodies with or without framework changes)). In one embodiment, the antibody or antigen-binding fragment thereof comprises the light chain CDRs (CDR1, CDR2 and CDR3) and heavy chain CDRs (CDR1, CDR2 and CDR3) of a particular immunoglobulin. In another embodiment, the antibody or antigen-binding fragment further comprises a human framework region.

The antibodies and antigen-binding fragments described herein can also be conjugated to an agent. In one embodiment, the agent is a label, for example, a radioisotope, an epitope label (tag), an affinity label (e.g., biotin, avidin), a spin label, an enzyme, a fluorescent group or a chemiluminescent group. Labeled antibodies or antigen-binding fragments of the present invention can be used, e.g., in the diagnostic, prognostic and/or screening methods described herein. In another embodiment, the antibody is conjugated to a drug, toxin or anti-inflammatory agent. Conjugation of a drug, toxin or anti-inflammatory agent to the anti-HMGB1 antibodies and antigen-binding fragments of the invention allows for targeting of these agents to sites of HMGB1 expression and/or activity. Drugs and toxins that can be conjugated to the antibodies of the present invention include, for example, chemotherapeutic agents (e.g., mitomycin C, paxlitaxol, methotrexate, 5-fluorouracil, cisplatin, cyclohexamide), toxins (e.g., ricin, gelonin) and other agents described herein (e.g., the agents described for combination therapy). Anti-inflammatory agents that can be conjugated include, e.g., those described herein and known in the art.

Antibodies that are specific for an HMGB1 polypeptide and/or fragment thereof (e.g., a mammalian (e.g., human) HMGB1 polypeptide and/or fragment thereof (e.g., Hp-16, Hp-31, Hp-91, Hp-106)) can be raised against an appropriate immunogen, such as an isolated and/or recombinant HMGB1 polypeptide or a fragment thereof (including synthetic molecules, such as synthetic peptides). Antibodies can also be raised by immunizing a suitable host (e.g., mouse) with cells (e.g., GH3 pituicytes, macrophage cells (e.g., RAW 246.7 cells, human macrophage cells), peripheral blood mononuclear cells (PBMCs (e.g., human PBMCs)), primary T cells (e.g., human primary T cells), adrenal cells (e.g., rat adrenal PC-12 cells, human adrenal cells), and kidney cells (e.g., rat primary kidney cells, human primary kidney cells)) that express an HMGB1 polypeptide. In addition, cells expressing a recombinant HMGB1 polypeptide or fragment thereof (e.g., a mammalian (e.g., human) HMGB1 polypeptide or fragment thereof), such as transfected cells, can be used as an immunogen or in a screen for an antibody that binds thereto (see e.g., Chuntharapai et al., *J. Immunol.*, 152: 1783-1789 (1994); Chuntharapai et al., U.S. Pat. No. 5,440,021).

Preparation of immunizing antigen, and polyclonal and monoclonal antibody production can be performed using any suitable technique. A variety of methods have been described (see e.g., Kohler et al., *Nature,* 256: 495-497 (1975) and *Eur. J. Immunol.* 6: 511-519 (1976); Milstein et al., *Nature* 266: 550-552 (1977); Koprowski et al., U.S. Pat. No. 4,172,124; Harlow, E. and D. Lane, 1988, *Antibodies: A Laboratory Manual,* (Cold Spring Harbor Laboratory: Cold Spring Harbor, N.Y.); *Current Protocols In Molecular Biology,* Vol. 2 (Supplement 27, Summer '94), Ausubel, F. M. et al., Eds., (John Wiley & Sons: New York, N.Y.), Chapter 11, (1991)). Generally, a hybridoma is produced by fusing a suitable immortal cell line (e.g., a myeloma cell line such as SP2/0, P3X63Ag8.653 or a heteromyeloma) with antibody-producing cells. Antibody-producing cells can be obtained from the peripheral blood or, preferably the spleen or lymph nodes, of humans or other suitable animals immunized with the antigen of interest. The fused cells (hybridomas) can be isolated using selective culture conditions, and cloned by limiting dilution. Cells that produce antibodies with the desired specificity can be selected by a suitable assay (e.g., ELISA).

Monoclonal antibodies that bind to HMGB1 are known in the art. For example, PCT Publication No. WO2005/026209 (the entire teachings of which are incorporated herein by reference) describe the production and characterization of particular monoclonal antibodies, including "6E6 HMGB1 mAb", "2E11 HMGB1 mAb", "6H9 HMGB1 mAb", "10D4 HMGB1 mAb" and "2G7 HMGB1 mAb".

Other suitable methods of producing or isolating antibodies of the requisite specificity (e.g., human antibodies or antigen-binding fragments) can be used, including, for example, methods that select recombinant antibody from a library (e.g., a phage display library). Transgenic animals capable of producing a repertoire of human antibodies (e.g., Xenomouse® (Abgenix, Fremont, Calif.)) can be produced using suitable methods (see e.g., Jakobovits et al., *Proc. Natl. Acad. Sci. USA,* 90: 2551-2555 (1993); Jakobovits et al., *Nature,* 362: 255-258 (1993)). Additional methods that are suitable for production of transgenic animals capable of producing a repertoire of human antibodies have been described (e.g., Lonberg et al., U.S. Pat. No. 5,545,806; Surani et al., U.S. Pat. No. 5,545,807; Lonberg et al., WO97/13852).

In one embodiment, the antibody or antigen-binding fragment thereof specifically binds to a fragment of an HMGB1 polypeptide (e.g., a fragment of a mammalian (e.g., human) HMGB1 polypeptide). As used herein, an antibody or antigen-binding fragment that "specifically binds to" or "has specificity for" a fragment of HMGB1 means that the antibody or antigen-binding fragment has an affinity for that fragment of HMGB1 that is greater than its affinity for other antigens. The phrases "specifically binds to" and "has specificity for" a fragment of HMGB1 can also refer to a binding reaction that is determinative of the presence of a target protein (e.g., HMGB1 or a fragment thereof) in a heterogeneous population of proteins and/or other biologics. Thus, under designated assay conditions, the antibodies and antigen-binding fragments of the invention bind preferentially to HMGB1 and/or fragments of HMGB1 and do not bind in a significant amount to other components present in a test sample.

In one embodiment, the antibody or antigen-binding fragment thereof specifically binds to a fragment of HMGB1, wherein the fragment of HMGB1 is selected from the group consisting of Hp-16 (SEQ ID NO:5), Hp-31 (SEQ ID NO:6), Hp-91 (SEQ ID NO:10) and Hp-106 (SEQ ID NO:11). In another embodiment, the antibody or antigen-binding fragment thereof specifically binds to a fragment of HMGB1, wherein the fragment of HMGB1 is selected from the group consisting of Hp-16 (SEQ ID NO:5), Hp-31 (SEQ ID NO:6), and Hp-91 (SEQ ID NO:10). In another embodiment, the antibody or antigen-binding fragment thereof specifically binds to Hp-16 (SEQ ID NO:5). In yet another embodiment, the antibody or antigen-binding fragment thereof specifically binds to Hp-31 (SEQ ID NO:6). In still another embodiment, the antibody or antigen-binding fragment thereof specifically binds to Hp-91 (SEQ ID NO:10). In a further embodiment, the antibody or antigen-binding fragment thereof specifically binds to Hp-106 (SEQ ID NO:11).

In one embodiment, the antibody or antigen-binding fragment thereof is an IgG or an antigen-binding fragment of an IgG. In another embodiment, the antibody or antigen-binding fragment thereof is an IgG1 or an antigen-binding fragment of an IgG1. In other embodiments, the antibody or antigen-binding fragment thereof is an IgG2a, IgG2b, IgG3 antibody, or an antigen-binding fragment of any of the foregoing.

As described and exemplified herein, particular fragments of HMGB1 (e.g., Hp-16 (SEQ ID NO:5), Hp-31 (SEQ ID NO:6), Hp-91 (SEQ ID NO:10) and Hp-106 (SEQ ID NO:11)) possess certain functional properties. Accordingly, antibodies and antigen-binding fragments that specifically bind to such HMGB1 fragments can inhibit (reduce or prevent) one or more of functions of an HMGB1 polypeptide or HMGB1 fragment. Such functions of HMGB1 or fragments of HMGB1 include, e.g., increasing inflammation (see, e.g., PCT Publication No. WO 02/092004; the entire teachings of which are incorporated herein by reference), increasing secretion or release of a cytokine (e.g., one or more proinflammatory cytokines) from a cell (e.g., as described herein and in PCT Publication No. WO 02/092004), binding to RAGE, binding to TLR2, binding to TLR4, chemoattraction (see, e.g., Degryse et al, *J. Cell Biol.* 152(6):1197-1206 (2001); the entire teachings of which are incorporated herein by reference), activation of antigen presenting cells (see, e.g., WO 03/026691; the entire teachings of which are incorporated herein by reference), stimulation of allogeneic T cells and induction of phenotypic and functional maturation of dendritic cells.

In particular embodiments, the antibodies and antigen-binding fragments of the invention inhibit release of a cytokine from a vertebrate cell treated with HMGB1. Such cytokines, the release of which can be inhibited by the antibodies and antigen-binding fragments of the invention, include, e.g., proinflammatory cytokines and other cytokines and chemokines (e.g, IL-6, IL-12, TNF-α, IL-18, IL-8, IL-2, IL-1β and/or IL-5). In one embodiment, the antibody or antigen-binding fragment inhibits the release of TNF-α from a vertebrate cell treated with HMGB1. As described herein and is known in the art, an antibody or antigen-binding fragment can be screened without undue experimentation for the ability to inhibit release of a cytokine (e.g., a proinflammatory cytokine) using standard methods.

In one embodiment, the antibody or antigen-binding fragment inhibits binding of a polypeptide (e.g., RAGE, TLR2, TLR4) to HMGB1. In another embodiment, the antibody or antigen-binding fragment inhibits induction of phenotypic and functional maturation of dendritic cells. In another embodiment, the antibody or antigen-binding fragment inhibits HMGB1-mediated stimulation of allogeneic T cells. In other embodiments, the antibodies and antigen-binding fragments inhibit one or more functions mediated by HMGB1 (e.g., one or more of the functions described herein).

In one embodiment, the antibody is a human antibody or an antigen-binding fragment thereof. In another embodiment, the antibody is a humanized antibody or an antigen-binding fragment thereof In another embodiment, the antibody is a chimeric antibody or antigen-binding fragment thereof. Ill still another embodiment, the antibody is a human antibody, a humanized antibody, a chimeric antibody or an antigen-binding fragment of any of the foregoing.

In certain embodiments, the antibodies or antigen-binding fragments thereof specifically bind to HMGB1 epitopes or antigenic determinants (e.g., epitopes present within HMGB1 and fragments of HMGB1 (e.g., epitopes present within Hp-16, Hp-31, Hp-91 or Hp-106)).

In one embodiment, the invention is a bispecific antibody, or functional fragment thereof (e.g., F(ab')$_2$), which binds to a fragment of HMGB1 (e.g., Hp-16, Hp-31, Hp-91 or Hp-106) and at least one other antigen (e.g., a tumor antigen, a viral antigen). Bispecific antibodies can be secreted by triomas and hybrid hybridomas. Generally, triomas are formed by fusion of a hybridoma and a lymphocyte (e.g., antibody-secreting B cell) and hybrid hybridomas are formed by fusion of two hybridomas. Each of the fused cells (i.e., hybridomas, lymphocytes) produces a monospecific antibody. However, triomas and hybrid hybridomas can produce an antibody containing antigen-binding sites that recognize different antigens. The supernatants of triomas and hybrid hybridomas can be assayed for bispecific antibody using a suitable assay (e.g., ELISA), and bispecific antibodies can be purified using conventional methods. (See, e.g., U.S. Pat. No. 5,959,084 (Ring et al.), U.S. Pat. No. 5,141,736 (Iwasa et al.), U.S. Pat. Nos. 4,444,878, 5,292,668, 5,523,210 (all to Paulus et al.) and U.S. Pat. No. 5,496,549 (Yamazaki et al.)).

In one embodiment, the invention relates to an isolated cell that produces an antibody or an antigen-binding fragment of the invention. In a particular embodiment, the isolated antibody-producing cell of the invention is an immortalized cell, such as a hybridoma, heterohybridoma, lymphoblastoid cell or a recombinant cell. The antibody-producing cells of the present invention have uses other than for the production of antibodies. For example, the cell of the present invention can be fused with other cells (such as suitably drug-marked human myeloma, mouse myeloma, human-mouse heteromyeloma or human lymphoblastoid cells) to produce, for example, additional hybridomas, and thus provide for the transfer of the genes encoding the antibody. In addition, the cell can be used as a source of nucleic acids encoding the anti-HMGB1 immunoglobulin chains, which can be isolated and expressed (e.g., upon transfer to other cells using any suitable technique (see e.g., Cabilly et al., U.S. Pat. No. 4,816,567, Winter, U.S. Pat. No. 5,225,539)). For instance, clones comprising a sequence encoding a rearranged anti-HMGB1 light and/or heavy chain can be isolated (e.g., by PCR). In addition, cDNA libraries can be prepared from mRNA isolated from an appropriate cell line, and cDNA clones encoding an anti-HMGB1 immunoglobulin chain(s) can be isolated. Thus, nucleic acids encoding the heavy and/or light chains of the antibodies, or portions thereof, can be obtained and used for the production of the specific immunoglobulin, immunoglobulin chain, or variants thereof (e.g., humanized immunoglobulins) in a variety of host cells or in an in vitro translation system. For example, the nucleic acids, including cDNAs, or derivatives thereof encoding variants such as a humanized immunoglobulin or immunoglobulin chain, can be placed into suitable prokaryotic or eukaryotic vectors (e.g., expression vectors) and introduced into a suitable host cell by an appropriate method (e.g., transformation, transfection, electroporation, infection), such that the nucleic acid is operably linked to one or more expression control elements (e.g., in the vector or integrated into the host cell genome), to produce a recombinant antibody-producing cell. Thus, in certain embodiments, the invention is a nucleic acid that encodes an antibody or antigen-binding fragment of the invention. In other embodiments, the invention is a vector that comprises a nucleic acid encoding an antibody or antigen-binding fragment of the invention.

Inhibiting Release of Proinflammatory Cytokines and Methods of Treatment

In one embodiment, the present invention is a method of inhibiting release of a cytokine (e.g., a proinflammatory cytokine) from a vertebrate (e.g., mammalian) cell. In one embodiment, the method comprises treating the cell with an antibody or antigen-binding fragment of the present invention.

As used herein, a "cytokine" is a soluble protein or peptide that is naturally produced by mammalian cells, which regulates immune responses and mediates cell-cell interactions. Cytokines can, either under normal or pathological conditions, modulate the functional activities of individual cells and tissues. A proinflammatory cytokine is a cytokine that is capable of causing one or more of the following physiological reactions associated with inflammation or inflammatory conditions: vasodilation, hyperemia, increased permeability of vessels with associated edema, accumulation of granulocytes and mononuclear phagocytes; and deposition of fibrin. In some cases, the proinflammatory cytokine can also cause apoptosis. For example, in chronic heart failure, it has been shown that TNF stimulates cardiomyocyte apoptosis (Pulkki, *Ann. Med.* 29:339-343 (1997); and Tsutsui, et al., *Immunol. Rev.* 174:192-209 (2000)). Nonlimiting examples of proinflammatory cytokines are tumor necrosis factor (TNF), interleukin (IL)-1α, IL-1β, IL-6, IL-8, IL-18, interferon γ, HMGB1, platelet-activating factor (PAF), and macrophage migration inhibitory factor (MIF). Other cytokines, the production and/or secretion of which can be inhibited by the antibodies and antigen-binding fragments of the invention, include those described and exemplified herein.

In one embodiment, the invention is a method of treating a condition in a subject, wherein the condition is characterized by activation of an inflammatory cytokine cascade comprising administering to the subject an antibody or antigen-binding fragment of the present invention.

In one embodiment, the method of treatment comprises administering to a subject a therapeutically effective amount of an antibody or antigen-binding fragment of the invention. As used herein, an "effective amount" or "therapeutically effective amount" is an amount sufficient to prevent or decrease an inflammatory response, and/or to ameliorate and/or decrease the longevity of symptoms associated with an inflammatory response. The amount of antibody or antigen-binding fragment that will be effective in the treatment, prevention or management of a particular condition can be determined, for example, by administering the composition to an animal model, such as those disclosed herein and/or known to those skilled in the art. In addition, in vitro assays may optionally be employed to help identify optimal dosage ranges.

Selection of the preferred effective dose can be determined (e.g., via clinical trials) by a skilled artisan based upon the consideration of several factors that are known to one of ordinary skill in the art. Such factors include, e.g., the condition or conditions to be treated, the severity of the subject's symptoms, the choice of antibody or antigen-binding fragment to be administered, the subject's age, the subject's body mass, the subject's immune status, the response of the individual subject, and other factors known by the skilled artisan to reflect the accuracy of administered pharmaceutical compositions.

The precise dose to be employed in the formulation will also depend on the route of administration, and the seriousness of the condition, and should be decided according to the judgment of the practitioner and each subject's circumstances. Effective doses may be extrapolated from dose-response curves derived from in vitro or animal model test systems. For example, using an in vivo cecal ligation and puncture (CLP) assay, a dose response assay for a particular anti-HMGB1 monoclonal antibody, namely 6E6 HMGB1 mAb, was performed (WO2005/026209).

For antibodies, the dosage administered to a subject (e.g., a human patient) is typically 0.1 mg/kg to 100 mg/kg of the subject's body weight. Preferably, the dosage administered to a subject is between 0.1 mg/kg and 20 mg/kg of the subject's body weight, more preferably 1 mg/kg to 10 mg/kg of the subject's body weight. In certain embodiments of the invention, the dosage is at least 1 mg/kg, or at least 5 mg/kg, or at least 10 mg/kg, or at least 50 mg/kg, or at least 100 mg/kg, or at least 150 mg/kg, of the subject's body weight. Generally, human and humanized antibodies have a longer half-life within the human body than antibodies from other species due to the immune response to foreign polypeptides. Thus, lower dosages of human antibodies and less frequent administration is often possible. For example, an effective amount of an antibody can range from about 0.01 mg/kg to about 5 or 10 mg/kg administered daily, weekly, biweekly or monthly.

Methods for determining whether an antibody or antigen-binding fragment inhibits an inflammatory condition are known to one skilled in the art. For example, inhibition of the release of a cytokine (e.g., a proinflammatory cytokine) from a cell can be measured according to methods known to one skilled in the art. For example, as described and exemplified herein, secretion or release of particular cytokines (e.g., IL-6, IL-12, TNF-α, IL-18, IL-8, IL-2, IL-1β, IL-5) from dendritic cells can be measured. In addition, TNF-α release from a cell can be measured using a standard murijie fibroblast L929 (ATCC, American Type Culture Collection, Rockville, Md.) cytotoxicity bioassay (Bianchi et al., *Journal of Experimental Medicine* 183:927-936 (1996)). The L929 cytotoxicity bioassay can be carried out as follows. RAW 264.7 cells are cultured in RPMI 1640 medium (Life Technologies, Grand Island, N.Y.) supplemented with 10% fetal bovine serum (Gemini, Catabasas, Calif.), and penicillin and streptomycin (Life Technologies). Polymyxin (Sigma, St. Louis, Mo.) is added at 100 units/ml to suppress the activity of any contaminating LPS. Cells are incubated with an antibody or antigen-binding fragment of the invention in Opti-MEM I medium for 8 hours, and conditioned supernatants (containing TNF-α that has been released from the cells) are collected. TNF-α that is released from the cells is measured by a standard murine fibroblast L929 (ATCC) cytotoxicity bioassay (Bianchi et al, supra) with the minimum detectable concentration of 30 pg/ml. Recombinant mouse TNF-α can be obtained from R&D Systems Inc. (Minneapolis, Minn.) and used as a control in these experiments. Methods for measuring release of other cytokines from cells are also known in the art.

An inflammatory condition that is suitable for the methods of treatment described herein can be one in which the inflammatory cytokine cascade is activated. In one embodiment, the inflammatory cytokine cascade causes a systemic reaction, such as with endotoxic shock. In another embodiment, the inflammatory condition is mediated by a localized inflammatory cytokine cascade, as in rheumatoid arthritis. Nonlimiting examples of inflammatory conditions that can be usefully treated using the antibodies and antigen-binding fragments of the present invention include, e.g., diseases involving the gastrointestinal tract and associated tissues (such as ileus, appendicitis, peptic, gastric and duodenal ulcers, peritonitis, pancreatitis, ulcerative, pseudomembranous, acute and ischemic colitis, diverticulitis, epiglottitis, achalasia, cholangitis, cholecystitis, coeliac disease, hepatitis, Crohn's disease, enteritis, and Whipple's disease); systemic or local inflammatory diseases and conditions (such as asthma, allergy, anaphylactic shock, immune complex disease, organ ischemia, reperfasion injury, organ necrosis, hay fever, sepsis, septicemia, endotoxic shock, cachexia, hyperpyrexia, eosinophilic granuloma, granulomatosis, and sarcoidosis); diseases involving the urogenital system and associated tissues (such as septic abortion, epididymitis, vaginitis, prostatitis, and urethritis); diseases involving the respiratory system and associated tissues (such as bronchitis, emphysema, rhinitis, cystic fibrosis, pneumonitis, adult respiratory distress syndrome, pneumoultramicroscopicsilicovolcanoconiosis, alvealitis, bronchiolitis, pharyngitis, pleurisy, and sinusitis); diseases arising from infection by various viruses (such as influenza, respiratory syncytial virus, HIV, hepatitis B virus, hepatitis C virus and herpes), bacteria (such as disseminated bacteremia, Dengue fever), fungi (such as candidiasis) and protozoal and multicellular parasites (such as malaria, filariasis, amebiasis, and hydatid cysts); dermatological diseases and conditions of the skin (such as burns, dermatitis, dernatomyositis, sunburn, urticaria warts, and wheals); diseases involving the cardiovascular system and associated tissues (such as stenosis, restenosis, vasulitis, angiitis, endocarditis, arteritis, atherosclerosis, thrombophlebitis, pericarditis, congestive heart failure, myocarditis, myocardial ischemia, periarteritis nodosa, and rheumatic fever); diseases involving the central or peripheral nervous system and associated tissues (such as Alzheimer's disease, meningitis, encephalitis, multiple sclerosis, cerebral infarction, cerebral embolism, Guillame-Barre syndrome, neuritis, neuralgia, spinal cord injury, paralysis, and uveitis); diseases of the bones, joints, muscles and connective tissues (such as the various arthritides and arthralgias, osteomyelitis, fasciitis, Paget's disease, gout, periodontal disease, rheumatoid arthritis, and synovitis); other autoimmune and inflammatory disorders (such as myasthenia gravis, thryoiditis, systemic lupus erythematosus, Goodpasture's syndrome, Behcets's syndrome, allograft rejection, graft-versus-host disease, Type I diabetes, anlylosing spondylitis, Berger's disease, and Retier's syndrome); as well as various cancers, tumors and proliferative disorders (such as Hodgkins disease); and, in any case the inflammatory or immune host response to any primary disease.

In one embodiment, the condition is selected from the group consisting of sepsis, allograft rejection, arthritis (e.g., rheumatoid arthritis), asthma, atherosclerosis, restenosis, lupus, adult respiratory distress syndrome, chronic obstructive pulmonary disease, psoriasis, pancreatitis, peritonitis, burns, myocardial ischemia, organic ischemia, reperfusion ischemia, Behcet's disease, graft versus host disease, Crohn's disease, ulcerative colitis, ileus, multiple sclerosis, and cachexia. In another embodiment, the condition is selected from the group consisting of sepsis, arthritis (e.g., rheumatoid arthritis), asthma, lupus, psoriasis, inflammatory bowel disease and Crohn's disease.

Preferably the antibodies and antigen-binding fragments are administered to a patient in need thereof in an amount sufficient to inhibit release of a proinflammatory cytokine from a cell and/or to treat an inflammatory condition. In one embodiment, release of the proinflammatory cytokine is inhibited by at least 10%, 20%, 25%, 50%, 75%, 80%, 90%, or 95%, as assessed using methods described herein and/or other methods known in the art.

The terms "therapy", "therapeutic" and "treatment", as used herein, refer to ameliorating symptoms associated with a disease or condition, for example, an inflammatory disease or an inflammatory condition, including preventing or delaying the onset of the disease symptoms, and/or lessening the severity or frequency of symptoms of the disease or condition.

The terms "subject" and "individual" are defined herein to include animals such as mammals, including but not limited to, primates, cows, sheep, goats, horses, dogs, cats, rabbits, guinea pigs, rats, mice or other bovine, ovine, equine, canine, feline, rodent, or murine species. In a preferred embodiment, the animal is a human.

In one embodiment, an excipient can be included with the antibodies and antigen-binding fragments of the invention. The excipient can be selected based on the expected route of administration of the antibodies or antigen-binding fragments in therapeutic applications. The route of administration of the composition depends on the condition to be treated. For example, intravenous injection may be preferred for treatment of a systemic disorder, such as endotoxic shock, and oral administration may be preferred to treat a gastrointestinal disorder, such as a gastric ulcer. As described above, the dosage of the antibody or antigen-binding fragment to be administered can be determined by the skilled artisan without undue experimentation in conjunction with standard dose-response studies. Depending on the condition, the antibody or antigen-binding fragment can be administered orally, parenterally, intranasally, vaginally, rectally, lingually, sub-lingually, bucally, intrabucally and/or transdermally to the patient.

Accordingly, antibodies or antigen-binding fragments designed for oral, lingual, sublingual, buccal and intrabuccal administration can be made without undue experimentation by means well known in the art, for example, with an inert diluent and/or edible carrier. The antibodies or antigen-binding fragments may be enclosed in gelatin capsules or compressed into tablets. For the purpose of oral therapeutic administration, the antibodies or antigen-binding fragments of the present invention may be incorporated with excipients and used in the form of tablets, troches, capsules, elixirs, suspensions, syrups, wafers, chewing gums, and the like.

Tablets, pills, capsules, troches, and the like, may also contain binders, recipients, disintegrating agent, lubricants, sweetening agents, and flavoring agents. Some examples of binders include microcrystalline cellulose, gum tragacanth, and gelatin. Examples of excipients include starch and lactose. Some examples of disintegrating agents include alginic acid, corn starch, and the like. Examples of lubricants include magnesium stearate and potassium stearate. An example of a glidant is colloidal silicon dioxide. Some examples of sweetening agents include sucrose, saccharin, and the like. Examples of flavoring agents include peppermint, methyl salicylate, orange flavoring, and the like. Materials used in preparing these various compositions should be pharmaceutically pure and non-toxic in the amounts used.

The antibodies and antigen-binding fragments of the present invention can be administered parenterally such as, for example, by intravenous, intramuscular, intrathecal or subcutaneous injection. Parenteral administration can be accomplished by incorporating the antibodies and antigen-binding fragments of the present invention into a solution or suspension. Such solutions or suspensions may also include sterile diluents, such as water for injection, saline solution, bacteriostatic saline (saline containing about 0.9% mg/ml benzyl alcohol), phosphate-buffered saline (referred to herein as PBS), Hank's solution, Ringer's-lactate, fixed oils, polyethylene glycols, glycerine, propylene glycol, and other synthetic solvents. Parenteral formulations may also include antibacterial agents (e.g., benzyl alcohol, methyl parabens), antioxidants (e.g., ascorbic acid, sodium bisulfite), and chelating agents (e.g., EDTA). Buffers, such as acetates, citrates or phosphates and agents for the adjustment of tonicity such as sodium chloride and dextrose, may also be added. The parenteral preparation can be enclosed in ampules, disposable syringes, or multiple dose vials made of glass or plastic.

Rectal administration includes administering the antibodies and antigen-binding fragments into the rectum or large intestine. This can be accomplished using suppositories or enemas. Suppository formulations can be made by methods known in the art. For example, suppository formulations can be prepared by heating glycerin to about 120° C., dissolving the antibody or antigen-binding fragment in the glycerin, mixing the heated glycerin, after which purified water may be added, and pouring the hot mixture into a suppository mold.

Transdermal administration includes percutaneous absorption of the antibody or antigen-binding fragment through the skin. Transdermal formulations include patches, ointments, creams, gels, salves, and the like.

The antibodies and antigen-binding fragments of the present invention can be administered nasally to a subject. As used herein, nasally administering or nasal administration, includes administering the antibodies or antigen-binding fragments to the mucous membranes of the nasal passage or nasal cavity of the subject. Pharmaceutical compositions for nasal administration of an antibody or antigen-binding fragment include therapeutically effective amounts of the antibody or antigen-binding fragment. Well-known methods for nasal administration include, for example, as a nasal spray, nasal drop, suspension, gel, ointment, cream, or powder. Administration of the antibody or antigen-binding fragment may also take place using a nasal tampon or nasal sponge.

As described above, a variety of routes of administration are possible including, for example, oral, dietary, topical, transdermal, rectal, parenteral (e.g., intravenous, intraarterial, intramuscular, subcutaneous, intradermal injection), and inhalation (e.g., intrabronchial, intranasal, oral inhalation, intranasal drops). Administration can be local or systemic as indicated. The preferred mode of administration can vary depending upon the antibody or antigen-binding fragment to be administered and the particular condition (e.g., disease) being treated, however, oral or parenteral administration is generally preferred.

If desired, the antibodies or antigen-binding fragments described herein can be administered with one or more additional agents (e.g., agents used to treat an inflammatory condition). The antibodies or antigen-binding fragments thereof and additional agent(s) can be present in a single composition or administered as separate compositions. If administered as separate compositions, the antibodies or antigen-binding fragments thereof and additional agent(s) can be co-administered or administered separately.

In one embodiment, the antibodies or antigen-binding fragments of the invention are administered with an anti-inflammatory agent. Such agents are known to one of skill in the art. In one embodiment, the agent is an antagonist of an early sepsis mediator. As used herein, an early sepsis mediator is a proinflammatory cytokine that is released from cells soon (i.e., within 30-60 min.) after induction of an inflammatory cytokine cascade (e.g., exposure to LPS). Nonlimiting examples of these cytokines are IL-1α, IL-1β, IL-6, PAF, and MIF. Also included as early sepsis mediators are receptors for these cytokines (for example, tumor necrosis factor receptor type 1) and enzymes required for production of these cytokines, for example, interleukin-1β converting enzyme). Antagonists of any early sepsis mediator, now known or later discovered, can be useful for these embodiments by further inhibiting an inflammatory cytokine cascade.

Nonlimiting examples of antagonists of early sepsis mediators are antisense compounds that bind to the mRNA of the early sepsis mediator, preventing its expression (see, e.g., Ojwang et al., *Biochemistry* 36:6033-6045 (1997); Pampfer et al., *Biol. Reprod.* 52:1316-1326 (1995); U.S. Pat. No. 6,228,642; Yahata et al, *Antisense Nucleic Acid Drug Dev.* 6:55-61 (1996); and Taylor et al., *Antisense Nucleic Acid Drug Dev.* 8:199-205 (1998)), ribozymes that specifically cleave the mRNA of the early sepsis mediator (see, e.g., Leavitt et al., *Antisense Nucleic Acid Drug Dev.* 10:409-414 (2000); Kisich et al., *J. Immunol.* 163(4):2008-2016 (1999); and Hendrix et al., *Biochem. J.* 314 (Pt. 2):655-661 (1996)), and antibodies that bind to the early sepsis mediator and inhibit their action (see, e.g., Kam and Targan, *Expert Opin. Pharmacother.* 1:615-622 (2000); Nagahira et al., *J. Immunol. Methods* 222:83-92 (1999); Lavine et al., J. Cereb. Blood Flow Metab. 18:52-58 (1998); and Holmes et al., *Hybridoma* 19:363-367 (2000)). The skilled artisan can determine the amount of early sepsis mediator to use for inhibiting any particular inflammatory cytokine cascade without undue experimentation with routine dose-response studies.

Other agents that can be administered with the antibodies and antigen-binding fragments of the invention include, e.g., Vitaxin™ and other antibodies targeting $\alpha v \beta 3$ integrin (see, e.g., U.S. Pat. No. 5,753,230, PCT Publication Nos. WO 00/78815 and WO 02/070007; the entire teachings of all of which are incorporated herein by reference) and anti-IL-9 antibodies (see, e.g., PCT Publication No. WO 97/08321; the entire teachings of which are incorporated herein by reference).

In one embodiment, the antibodies and antigen-binding fragments of the invention are administered with inhibitors of TNF biological activity (e.g., inhibitors of TNF-$\alpha$ biological activity). Such inhibitors of TNF activity include, e.g., peptides, proteins, synthesized molecules, for example, synthetic organic molecules, naturally-occurring molecule, for example, naturally occurring organic molecules, nucleic acid molecules, and components thereof. Preferred examples of agents that inhibit TNF biological activity include infliximab (Remicade®; Centocor, Inc., Malvern, Pa.), etanercept (Enbrel®; Immunex; Seattle, Wash.), adalimumab (Humira®; D2E7; Abbot Laboratories, Abbot Park Ill.), CDP870 (Pharmacia Corporation; Bridgewater, N.J.) CDP571 (Celltech Group plc, United Kingdom), Lenercept (Roche, Switzerland), and Thalidomide.

In certain embodiments, the present invention is directed to a composition comprising the antibody or antigen-binding fragments described herein, in a pharmaceutically-acceptable excipient. As described above, the excipient included with the antibody or antigen-binding fragment in these compositions is selected based on the expected route of administration of the composition. Suitable pharmaceutically-acceptable excipients include those described above and known in the art.

In one embodiment, the invention is directed to an aptamer of HMGB1 and/or a fragment of HMGB1 (e.g., an aptamer of Hp-16, Hp-31, Hp-91 or Hp-106). As is known in the art, aptamers are macromolecules composed of nucleic acid (e.g., RNA, DNA) that bind tightly to a specific molecular target (e.g., an HMGB1 polypeptide or fragment thereof). A particular aptamer may be described by a linear nucleotide sequence and is typically about 15-60 nucleotides in length. The chain of nucleotides in an aptamer form intramolecular interactions that fold the molecule into a complex three-dimensional shape, and this three-dimensional shape allows the aptamer to bind tightly to the surface of its target molecule. Given the extraordinary diversity of molecular shapes that exist within the universe of all possible nucleotide sequences, aptamers may be obtained for a wide array of molecular targets, including proteins and small molecules. In addition to high specificity, aptamers have very high affinities for their targets (e.g., affinities in the picomolar to low nanomolar range for proteins). Aptamers are chemically stable and can be boiled or frozen without loss of activity. Because they are synthetic molecules, they are amenable to a variety of modifications, which can optimize their function for particular applications. For example, aptamers can be modified to dramatically reduce their sensitivity to degradation by enzymes in the blood for use in in vivo applications. In addition, aptamers can be modified to alter their biodistribution or plasma residence time.

Selection of apatmers that can bind HMGB1 or a fragment of HMGB1 (e.g., Hp-16, Hp-31, Hp-91 or Hp-106) can be achieved through methods known in the art. For example, aptamers can be selected using the SELEX (Systematic Evolution of Ligands by Exponential Enrichment) method (Tuerk, C., and Gold, L., *Science* 249:505-510 (1990)). In the SELEX method, a large library of nucleic acid molecules (e.g., $10^{15}$ different molecules) is produced and/or screened with the target molecule (e.g., a fragment of HMGB1). The target molecule is allowed to incubate with the library of nucleotide sequences for a period of time. Several methods, which are known in the art, can then be used to physically isolate the aptamer target molecules from the unbound molecules in the mixture, which can be discarded. The aptamers with the highest affinity for the target molecule can then be purified away from the target molecule and amplified enzymatically to produce a new library of molecules that is substantially enriched for aptamers that can bind the target molecule. The enriched library can then be used to initiate a new cycle of selection, partitioning, and amplification. After 5-15 cycles of this iterative selection, partitioning and amplification process, the library is reduced to a small number of aptamers that bind tightly to the target molecule. Individual molecules in the mixture can then be isolated, their nucleotide sequences determined, and their properties with respect to binding affinity and specificity measured and compared. Isolated aptamers can then be further refined to eliminate any nucleotides that do not contribute to target binding and/or aptamer structure, thereby producing aptamers truncated to their core binding domain. See Jayasena, S. D. *Clin. Chein.* 45:1628-1650 (1999) for review of aptamer technology; the entire teachings of which are incorporated herein by reference).

In particular embodiments, the aptamers of the invention have the binding specificity and/or functional activity described herein for the antibodies and antigen-binding fragments of the invention. Thus, for example, in certain embodiments, the present invention is drawn to aptamers that have the same or similar binding specificity as described herein for the antibodies of the invention (e.g., binding specificity for Hp-16, Hp-31, Hp-91 or Hp-106). In particular embodiments, the aptamers of the invention can bind to a fragment of HMGB1 (e.g., Hp-16, Hp-31, Hp-91 or Hp-106) and inhibit one or more functions of the HMGB1 polypeptide. Such HMGB1 functions include, e.g., those described herein (e.g., increasing inflammation, increasing secretion or release of a cytokine (e.g., one or more proinflammatory cytokines) from a cell, binding to RAGE, binding to TLR2, binding to TLR4, chemoattraction, activation of antigen presenting cells, stimulation of allogeneic T cells, and induction of phenotypic and functional maturation of dendritic cells.

Methods of Diagnosis and/or Prognosis

In another embodiment, the invention is a diagnostic and/or prognostic method for detecting an HMGB1 polypeptide or a fragment thereof in a sample. In this embodiment, a sample is contacted with an antibody or antigen-binding fragment of the present invention, under conditions suitable for binding of the antibody or antigen-binding fragment to HMGB1 or a fragment of HMGB1 present in the sample. The method further comprises detecting antibody-HMGB1 complexes, antigen-binding fragment-HMGB1 complexes, antibody-HMGB1 fragment complexes or antigen-binding fragment-HMGB1 fragment complexes, wherein detection of such complexes is indicative of the presence of an HMGB1 polypeptide or fragment thereof in the sample.

In another embodiment, the antibody or antigen-binding fragment comprises a detectable label. Labels suitable for use in detection of a complex between an HMGB1 polypeptide or fragment thereof and an antibody or antigen-binding fragment include, for example, a radioisotope, an epitope label (tag), an affinity label (e.g., biotin, avidin), a spin label, an enzyme, a fluorescent group or a chemiluminescent group.

As described herein, the antibodies and antigen-binding fragments can be used to detect or measure expression of an HMGB1 polypeptide. For example, antibodies and antigen-binding fragments of the present invention can be used to detect or measure an HMGB1 polypeptide in a biological sample (e.g., cells, tissues or body fluids from an individual, such as blood, serum, leukocytes (e.g., activated T lymphocytes), bronchoalveolar lavage fluid, saliva, bowel fluid, synovial fluid, biopsy specimens). In one embodiment, the sample is blood or serum. For example, a sample (e.g., tissue and/or fluid) can be obtained from an individual and a suitable assay can be used to assess the presence or amount of an HMGB1 polypeptide. Suitable assays include immunological and immunochemical methods, such as flow cytometry (e.g., FACS analysis) and immunosorbent assays, including enzyme-linked immunosorbent assays (ELISA), radioimmunoassay (RIA), chemiluminescence assays, immunoblot (e.g., western blot), immunocytochemistry and immunohistology. Generally, a sample and an antibody or antigen-binding fragment of the present invention are combined under conditions suitable for the formation of a complex between an HMGB1 polypeptide and the antibody or antigen-binding fragment thereof, and the formation of said complex is assessed (directly or indirectly). In one embodiment, diagnosis and/or prognosis is done using ELISA and/or western blot analysis.

As in known in the art, the presence of an increased level of an HMGB1 polypeptide in a sample (e.g., a tissue sample) obtained from an individual can be a diagnostic and/or prognostic indicator for monitoring the severity and predicting the likely clinical course of sepsis for a subject exhibiting symptoms associated with conditions characterized by activation of the inflammatory cascade (see U.S. Pat. No. 6,303,321, the entire teachings of which are incorporated herein by reference). Thus, in one embodiment, the antibodies and antigen-binding fragments of the invention can be used in diagnostic and prognostic methods for monitoring the severity and/or predicting the likely clinical course of an inflammatory condition associated with HMGB1 expression (e.g., the conditions described herein). In certain embodiments, the diagnostic and/or prognostic methods comprise measuring the concentration of HMGB1 in a sample, preferably a serum sample, and comparing that concentration to a standard for HMGB1 that is representative of a normal concentration range of HMGB1 in a like sample. In this method, a higher level of HMGB1 is indicative of poor prognosis and/or the likelihood of toxic reactions. The diagnostic method may also be applied to other tissue or fluid compartments, such as cerebrospinal fluid or urine.

In another embodiment, the invention is a test kit for use in detecting the presence of an HMGB1 polypeptide or fragment thereof in a sample. Such test kits can comprise, e.g., an antibody or antigen-binding fragment of the invention and one or more ancillary reagents suitable for detecting the presence of a complex between the antibody or antigen-binding fragment and an HMGB1 polypeptide or fragment thereof. The antibody and antigen-binding fragments of the present invention can be provided in lyophilized form, either alone or in combination with additional antibodies specific for other epitopes. The antibodies or antigen-binding fragments thereof, which can be labeled or unlabeled, can be included in the kits with adjunct ingredients (e.g., buffers, such as Tris (Tris(hydroxymethyl)aminomethane), phosphate and carbonate, stabilizers, excipients, biocides and/or inert proteins, e.g., bovine serum albumin). For example, the antibodies or antigen-binding fragments can be provided as a lyophilized mixture with the adjunct ingredients, or the adjunct ingredients can be separately provided for combination by the user. Generally these adjunct materials will be present in less than about 5% by weight based on the amount of active antibody, and usually will be present in a total amount of at least about 0.001% by weight based on antibody concentration. Where a second antibody or antigen-binding fragment capable of binding to the anti-HMGB1 antibody or antigen-binding fragment is employed, such antibody or antigen-binding fragment can be provided in the kit, for instance in a separate vial or container. The second antibody or antigen-binding fragment, if present, is typically labeled, and can be formulated in an analogous manner with the antibody formulations described above. The antibodies, antigen-binding fragments and/or ancillary reagent of the kit can be packaged separately or together within suitable containment means (e.g., bottle, box, envelope, tube). When the kit comprises a plurality of individually packaged components, the individual packages can be contained within a single larger containment means (e.g., bottle, box, envelope, tube).

Methods of Screening

In another embodiment, the invention is a method of detecting and/or identifying an agent that binds to an HMGB1 polypeptide or fragment thereof and inhibits release of a cytokine from a vertebrate cell treated with HMGB1. In this method, an antibody or antigen-binding fragment of the invention, a test agent and a composition comprising an HMGB1 polypeptide or fragment thereof are combined, and complex formation between the antibody or antigen-binding fragment and the HMGB1 polypeptide or fragment thereof is measured. A decrease in the formation of such complex indicates that the test agent binds to the HMGB1 polypeptide or fragment thereof. Thus, in this embodiment, the method of detecting or identifying an agent that binds to an HMGB1 polypeptide is a competitive binding assay in which the ability of a test agent to inhibit the binding of an antibody or antigen-binding fragment of the invention is assessed. For example, in one embodiment, the antibody or antigen-binding fragment can be labeled with a suitable label (e.g., as described herein) and the amount of labeled antibody or antigen-binding fragment required to saturate the HMGB1 polypeptide of fragment thereof present in the assay can be determined. For example, a saturating amount of labeled antibody or antigen-binding fragment and various amounts of a test agent can be contacted with an HMGB1 polypeptide under conditions suitable for binding, and complex formation determined. In another embodiment, the HMGB1 polypeptide can be labeled. Suitable labels for labeling antibodies, antigen-binding fragments and/or HMGB1 polypeptides include those described above.

A variety of agents, such as proteins (e.g., antibodies), peptides, peptidomimetics, small organic molecules, nucleic acids and the like, can be tested for binding to an HMGB1 polypeptide of fragment thereof. According to the method of the present invention, agents can be individually screened or one or more agents can be tested simultaneously. Where a mixture of compounds is tested, the compounds selected by the processes described can be separated (as appropriate) and, identified using suitable methods (e.g., sequencing, chromatography). The presence of one or more compounds (e.g., a ligand, inhibitor, promoter) in a test sample can also be determined according to these methods.

Agents that bind to an HMGB1 polypeptide that are useful in the therapeutic methods described herein can be identified, for example, by screening libraries or collections of molecules (e.g., the Chemical Repository of the National Cancer Institute, in assays described herein or using other suitable methods. Libraries, such as combinatorial libraries, of compounds (e.g., organic compounds, recombinant or synthetic peptides, "peptoids", nucleic acids) produced by combinatorial chemical synthesis or other methods can be tested (see e.g., Zuckerman, R. N. et al., *J. Med. Chem.*, 37: 2678-2685 (1994) and references cited therein; see also, Ohlmeyer, M. H. J. et al., *Proc. Natl. Acad. Sci. USA* 90:10922-10926 (1993) and DeWitt, S. H. et al., *Proc. Natl. Acad. Sci. USA* 90:6909-6913 (1993), relating to tagged compounds; Rutter, W. J. et al. U.S. Pat. No. 5,010,175; Huebner, V. D. et al., U.S. Pat. No. 5,182,366; and Geysen, H. M., U.S. Pat. No. 4,833,092). Where compounds selected from a library carry unique tags, identification of individual compounds by chromatographic methods is possible.

The present invention will now be illustrated by the following Examples, which is not intended to be limiting in any way. The relevant teachings of all publications cited herein that have not explicitly been incorporated herein by reference, are incorporated herein by reference in their entirety.

Example 1

Four 18 Amino Acid HMGB1 Peptides Induce Cytokine Secretion in Human and Murine Dendritic Cells Materials and Methods:
Generation of Human Dendritic Cells (DCs)

Peripheral blood mononuclear cells (PBMCs) were isolated from the blood of normal volunteers (Long Island Blood Services, Melville, N.Y.) over a Ficoll-Hypaque (Amersham Biosciences, Uppsala, Sweden) density gradient. $CD14^+$ monocytes were isolated from PBMCs by positive selection using anti-CD14 beads (Miltenyi Biotech., Auburn, Calif.), following the manufacturer's instructions. To generate DCs, $CD14^+$ cells were cultured in RPMI 1640 medium supplemented with 2 mM L-glutamine (GIBCO-BRL Life Technologies, Grand Island, N.Y.), 50 µM 2-mercaptoethanol (Sigma, St. Louis, Mo.), 10 mM HEPES (GIBCO-BRL), penicillin (100 U/ml), streptomycin (100 µg/ml) (GIBCO-BRL), and 5% human AB serum (Gemini Bio-Products, Woodland, Calif.). Cultures were maintained for 7 days in 6-well trays ($3 \times 10^6$ cells/well) supplemented with 1000 U GM-CSF per ml (Immunex, Seattle, Wash.) and 200 U IL-4 per ml (R&D Systems, Minneapolis, Minn.) at days 0, 2, 4 and 6.

Generation of Mouse DCs

Bone marrow-derived DCs (BM-DCs) were generated using modifications of the original method described by Inaba, et al. (*J. Exp. Med.* 1 76:1693-1702 (1992)). In brief, bone marrow suspensions were incubated with red cell lysis buffer (PUREGENE™ RBC Lysis Solution, Gentra Systems, Minneapolis, Minn.) to remove red blood cells. After washing in media, lymphocytes and Ia-positive cells were killed with a cocktail of monoclonal antibodies (mAbs) and rabbit complement for 60 min at 37° C. The mAbs that were used were GK1.5 anti-CD4, TIB211 anti-CD8, TIB 120 anti-Ia, and TIB 146 anti B220 (these mAbs were kindly provided by Dr. Ralph Steinman). The cells were subsequently cultured in media containing 5% FCS and 10 ng/ml recombinant mouse GM-CSF (R&D Systems, Minneapolis, Minn.) for 7 days. For some experiments, the cells were further purified at day 7 using $CD11c^+$-microbeads (Miltenyi Biotech., Auburn, Calif.), according to the manufacturer's instructions.

Reagents

Recombinant HMGB1-B box domain (HMGB1-Bx) was expressed in *Escherichia coli* and purified as described by Li, et al. (*Mol. Med.* 9:37-45; *J. Immunol. Methods* 289:211-223 (2004)). Purified HMGB1-Bx contained trace amounts of LPS (19 pg LPS/µg HMGB1-Bx) as measured by the chromogenic *Limulus* amebocyte lysate assay (BioWhittacker Inc, Walkersville, Md.). All experiments using HMGB1-Bx, as well as the HMGB1 peptides, were performed in the presence of polymyxin B (200 U/ml) to neutralize the amount of contaminating LPS in the HMGB1-Bx and peptide preparations. We have previously shown that the DC stimulatory capacity of HMGB1-Bx requires an intact tertiary structure and is not due to contaminating amounts of LPS, as trypsinization abolished HMGB1-Bx activity (Messmer, et al., *J. Immunol.* 173: 307-313 (2004); the entire teachings of which are incorporated herein by reference).

Treatment of Dendritic Cells and Measurements of Cytokines and Chemokines

Secreted cytokine/chemokine levels were measured by ELISA (Pierce Boston Technology Center, SearchLight™ Proteome Arrays Multiplex Sample Testing Services, Woburn, Mass.) 48 h after addition of the various peptides. Polymyxin B (200 U/ml) was added to all cultures, except those containing LPS, before the stimuli were added. Immature monocyte-derived human dendritic cells (DCs) and immature bone-marrow derived murine dendritic cells (BM-DCs) were cultured either in the presence of HMGB1 peptides (200 µg/ml), whose sequences map to different regions of the HMGB1 protein (see Table 1), the entire HMGB1 B-box domain (HMGB1-Bx) (50 µg/ml), or LPS (100 ng/ml). Untreated cells (medium) were tested as a control. Each peptide was named according to the corresponding position of its first amino acid within the full-length HMGB1 sequence. All peptides were N-terminally biotinylated except "Hp-106 (non bio)".

TABLE 1

Amino Acid Sequences of HMGB1 Peptides

| Peptide | Amino Acid sequence | |
|---|---|---|
| Hp-1 | MGKGDPKKPRGKMSSYAF | (SEQ D NO: 4) |
| Hp-16 | YAFFVQTCREEHIKKHPD | (SEQ ID NO: 5) |
| Hp-31 | HPDASVNFSEFSKKCSER | (SEQ ID NO: 6) |
| Hp-46 | SERWKTMSAKEKGKFEDM | (SEQ ID NO: 7) |

TABLE 1-continued

Amino Acid Sequences of HMGB1 Peptides

| Peptide | Amino Acid sequence | |
|---|---|---|
| Hp-61 | EDMAKADKARYEREMKTY | (SEQ ID NO: 8) |
| Hp-76 | KTYIPPKGETKKKFKDPN | (SEQ ID NO: 9) |
| Hp-91 | DPNAPKRPPSAFFLFCSE | (SEQ ID NO: 10) |
| Hp-106 | CSEYRPKIKGEHPGLSIG | (SEQ ID NO: 11) |
| Hp-113 | IKGEHPGLSIGDVAKKLG | (SEQ ID NO: 12) |
| Hp-121 | SIGDVAKKLGEMWNNTAA | (SEQ ID NO: 13) |
| Hp-133 | WNNTAADDKQPYEKKAAK | (SEQ ID NO: 14) |
| Hp-136 | TAADDKQPYEKKAAKLKE | (SEQ ID NO: 15) |
| Hp-151 | LKEKYEKDIAAYRAKGKP | (SEQ ID NO: 16) |
| Hp-166 | GKPDAAKKGVVKAEKSKK | (SEQ ID NO: 17) |
| Hp-181 | SKKKKEEEEDEEDEEDEE | (SEQ ID NO: 18) |
| Hp-196 | DEEEEEDEEDEDEEEDDDDE | (SEQ D NO: 19) |

Results

Figure 1B:
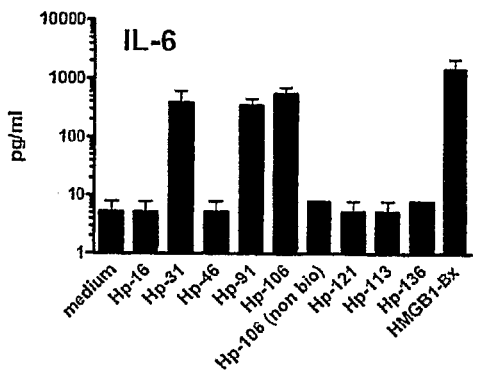
FIG. 1B is a bar graph depicting the quantity of the cytokine, IL-6, which is secreted by human immature monocyte-derived dendritic cells (DCs) following stimulation with either Hp-31, Hp-106, peptides that flank these sequences, or the entire B-box domain (HMGB1-Bx). Untreated cells (medium) were included as a control. Results represent the mean+/− SEM of three independent experiments, which were conducted using DCs that were generated from different donors.
Figure 1C:
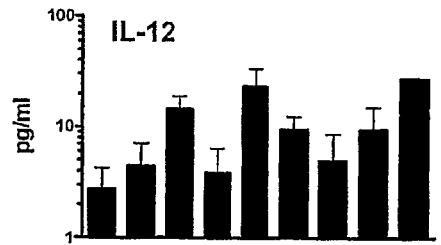
FIG. 1C is a bar graph depicting the quantity of the cytokine, IL-12, which is secreted by human immature monocyte-derived dendritic cells (DCs) following stimulation with either Hp-31, Hp-106, peptides that flank these sequences, the entire B-box domain (HMGB1-Bx), or LPS. Untreated cells (medium) were included as a control. Results represent the mean+/− SEM of two independent experiments using DCs generated from different donors.
Figure 1D:
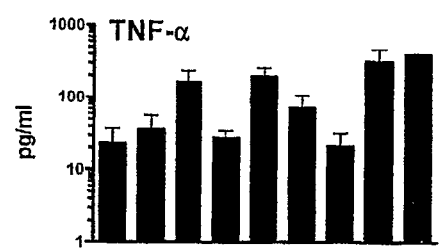
FIG. 1D is a bar graph depicting the quantity of the cytokine, TNF-α, which is secreted by human immature monocyte-derived dendritic cells (DCs) following stimulation with either Hp-31, Hp-106, peptides that flank these sequences, the entire B-box domain (HMGB1-Bx), or LPS. Untreated cells (medium) were included as a control. Results represent the mean+/− SEM of two independent experiments using DCs generated from different donors.
Figure 1E:
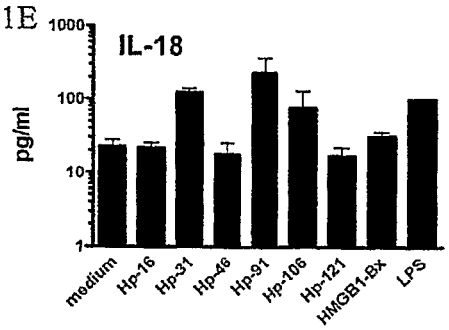
FIG. 1E is a bar graph depicting the quantity of the cytokine, IL-18, which is secreted by human immature monocyte-derived dendritic cells (DCs) following stimulation with either Hp-31, Hp-106, peptides that flank these sequences, the entire B-box domain (HMGB1-Bx), or LPS. Untreated cells (medium) were included as a control. Results represent the mean+/− SEM of two independent experiments using DCs generated from different donors.
Figure 1F:
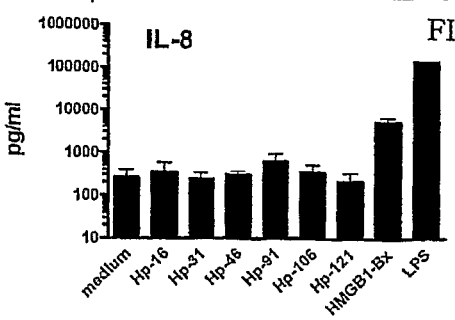
FIG. 1F is a bar graph depicting the quantity of the cytokine, IL-8, which is secreted by human immature monocyte-derived dendritic cells (DCs) following stimulation with either Hp-31, Hp-106, peptides that flank these sequences, the entire B-box domain (HMGB1-Bx), or LPS. Untreated cells (medium) were included as a control. Results represent the mean+/− SEM of two independent experiments using DCs generated from different donors.

It has been shown previously that an 18 amino acid peptide, whose sequence corresponds to a part of the B box domain of HMGB1, induced IL-6 secretion in human monocyte-derived DCs (Messmer, et al., *J. Immunol.* 173: 307-313 (2004)). In order to identify other peptides that induce cytokine secretion, various 18 amino acid HMGB1 peptides that span the whole HMGB1 molecule (see Table 1) were tested. Peptides Hp-31 and Hp-106 induced secretion of IL-6 by DCs (FIG. 1A). Subsequently, peptides that overlap by three amino acids with either the N- or C-terminus of these two peptides were tested. Hp-91, a C-terminal flanking peptide of Hp-106, which shares only three amino acids (namely CSE; see Table 1) with Hp-106, also enhanced IL-6 secretion by DCs (FIG. 1B). In contrast, two peptides that flank and partially overlap with Hp-31 (i.e., Hp-16 and Hp-46) did not induce IL-6 secretion when tested (FIG. 1B). An Hp-106 peptide that was not biotinylated at its N-terminus also failed to stimulate IL-6 secretion, indicating that N-terminal biotinylation is required for the DC-stimulatory effect of the active peptide (see FIG. 1B, labeled as "Hp-106 (non bio)"). Stimulation of IL-6 secretion, however, was not caused by biotin, because several different peptides that were N-terminally biotinylated did not stimulate secretion of IL-6 by DCs (FIGS. 1A and 1B). In addition, three peptides, Hp-31, Hp-91, and Hp-106, which induced IL-6 secretion, also induced secretion of IL-12 (p 70) (FIG. 1C), TNF-α (FIG. 1D), and IL-18 (FIG. 1E), but did not induce secretion of IL-8 (FIG. 1F). In contrast, HMGB1-Bx enhanced production of IL-8, but not IL-18 (FIGS. 1E and 1F). Neither HMGB1-Bx-treated DCs, nor the peptide-treated DCs, showed enhanced secretion of IL-10 (Table 2) or TGF-β.

Figure 2A:
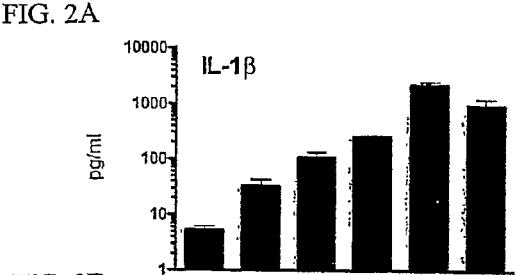
FIG. 2A is a bar graph depicting the quantity of IL-1β that is secreted by murine bone marrow-derived dendritic cells (BM-DCs) following stimulation with a particular HMGB1-derived peptide (Hp-16, Hp-91 or Hp-106), the entire B-box domain (HMGB1-Bx), or LPS. Untreated cells (medium) were included as a control. Results represent the mean+/− SEM of three independent experiments, which were conducted using DCs that were generated from different donors.
Figure 2B:
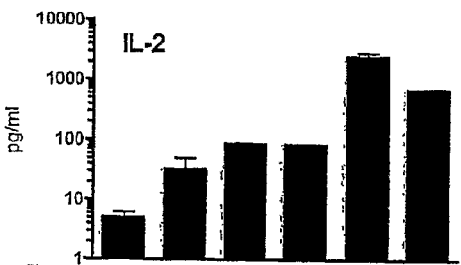
FIG. 2B is a bar graph depicting the quantity of IL-12 that is secreted by murine bone marrow-derived dendritic cells (BM-DCs) following stimulation with a particular HMGB1-derived peptide (Hp-16 or Hp-106), the entire B-box domain (HMGB1-Bx), or LPS. Untreated cells (medium) were included as a control. Results represent the mean+/− SEM of three independent experiments, which were conducted using DCs that were generated from different donors.
Figure 2C:
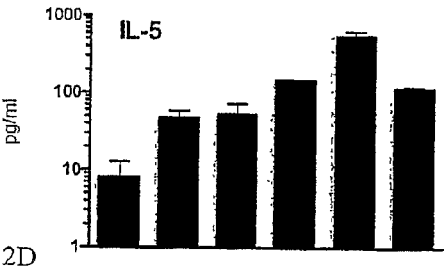
FIG. 2C is a bar graph depicting the quantity of IL-2 that is secreted by murine bone marrow-derived dendritic cells (BM-DCs) following stimulation with a particular HMGB1-derived peptide (Hp-16, Hp-91 or Hp-106), the entire B-box domain (HMGB1-Bx), or LPS. Untreated cells (medium) were included as a control. Results represent the mean+/− SEM of three independent experiments, which were conducted using DCs that were generated from different donors.
Figure 2D:
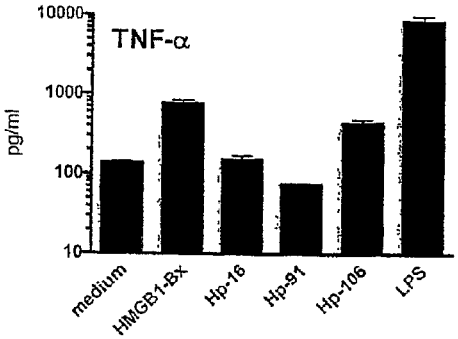
FIG. 2D is a bar graph depicting the quantity of IL-8 that is secreted by murine bone marrow-derived dendritic cells (BM-DCs) following stimulation with a particular HMGB1-derived peptide (Hp-16 or Hp-106), the entire B-box domain (HMGB1-Bx), or LPS. Untreated cells (medium) were included as a control. Results represent the mean+/− SEM of three independent experiments, which were conducted using DCs that were generated from different donors.
Figure 2E:
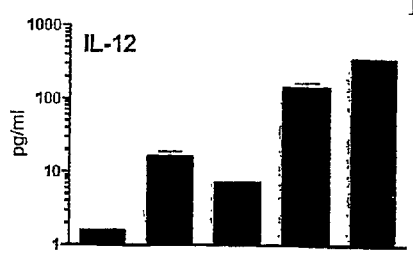
FIG. 2E is a bar graph depicting the quantity of IL-5 that is secreted by murine bone marrow-derived dendritic cells (BM-DCs) following stimulation with a particular HMGB1-derived peptide (Hp-16, Hp-91 or Hp-106), the entire B-box domain (HMGB1-Bx), or LPS. Untreated cells (medium) were included as a control. Results represent the mean+/− SEM of three independent experiments, which were conducted using DCs that were generated from different donors.
Figure 2F:
FIG. 2F is a bar graph depicting the quantity of IL-18 that is secreted by murine bone marrow-derived dendritic cells (BM-DCs) following stimulation with a particular HMGB1-derived peptide (Hp-16 or Hp-106), the entire B-box domain (HMGB1-Bx), or LPS. Untreated cells (medium) were included as a control. Results represent the mean+/− SEM of three independent experiments, which were conducted using DCs that were generated from different donors.
Figure 2G:
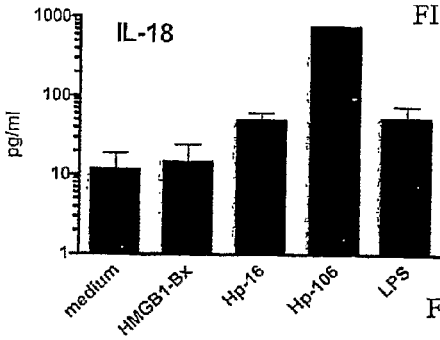
FIG. 2G is a bar graph depicting the quantity of TNF-α that is secreted by murine bone marrow-derived dendritic cells (BM-DCs) following stimulation with a particular HMGB1-derived peptide (Hp-16, Hp-91 or Hp-106), the entire B-box domain (HMGB1-Bx), or LPS. Untreated cells (medium) were included as a control. Results represent the mean+/− SEM of three independent experiments, which were conducted using DCs that were generated from different donors.

Murine BM-DCs that were exposed to HMGB1-Bx displayed enhanced secretion of IL-1β, IL-2, IL-5, TNF-α, IL-12 (p70), and IL-8 (FIGS. 2A-2E and 2G), but not IL-18 (FIG. 2F). In contrast to human DCs, HMGB1-Bx-stimulated murine BM-DCs did not show enhanced secretion of IL-6 (Table 2). The three HMGB1 peptides that induced cytokine secretion by human DCs (i.e., Hp-106, Hp-91 and Hp-31), also induced cytokine secretion by murine BM-DCs. In addition, Hp-16, which did not stimulate cytokine secretion in human DCs, enhanced cytokine secretion in murine BM-DCs. Hp-16 and Hp-106 enhanced secretion of IL-1β, IL-2, IL-5, IL-12, and IL-18 (FIGS. 2A-2C, 2E and 2G), but only Hp-106 enhanced secretion of IL-8 and TNF-α (FIGS. 2D and 2G). IL-18 production was enhanced by exposure of BM-DCs to either Hp-16 or Hp-106, but not to HMGB1-Bx (FIG. 2F). Hp-91, which enhanced cytokine secretion in human DCs, also increased production of IL-1β, IL-2, and IL-5 (FIGS. 2A, 2C and 2E), but not of TNF-α (FIG. 2G), IL-18, or IL-8 in BM-DCs.

Figure 2H:
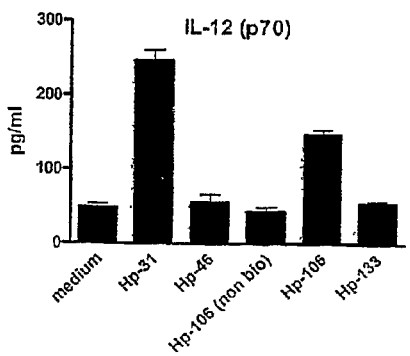
FIG. 2H is a bar graph depicting the quantity of IL-12 (p70) that is secreted by murine bone marrow-derived dendritic cells (BM-DCs), following stimulation with a particular HMGB1-derived peptide (Hp-31, Hp-46, non-biotinylated Hp-106 (Hp-106 (non bio)) or Hp-106). All peptides tested were biotinylated at the N-terminus, with the exception of non-biotinylated Hp-106 (Hp-106 (non bio)). Untreated cells (medium) were included as a control. Results represent the mean+/− SEM of three independent experiments, which were conducted using DCs that were generated from different donors.

Hp-31 enhanced the production of IL-12 (p70) (FIG. 2H), IL-2, IL-5, and IL-1β, but not IL-6 and IL-10 (Table 2) in murine BM-DCs. Furthermore, as observed for human DCs, N-terminal biotinylation was required to stimulate cytokine secretion. The non-biotinylated Hp-106 peptide ("Hp-106 (non-bio)") did not enhance IL-12 secretion (FIG. 2H). The DC stimulatory capacity of the peptides was dependent on the peptide sequence and not biotin, because certain biotinylated peptides did not enhance IL-12 secretion (FIG. 2H).

TABLE 2

Profile of Cytokine Secretion in Human and Murine Dendritic Cells Following Stimulation with HMGB1-Bx or Select HMGB1 Peptides.

| | HUMAN DC | | | | | | MURINE DC | | | | |
|---|---|---|---|---|---|---|---|---|---|---|---|
| | HMGB1-Bx | Hp-16 | Hp-31 | Hp-91 | Hp-106 | | HMGB1-Bx | Hp-16 | Hp-31 | Hp-91 | Hp-106 |
| IL-6 | + | − | + | + | + | IL-6 | − | − | − | − | − |
| IL-12 | + | − | + | + | + | IL-12 | + | + | + | + | + |
| TNFα | + | − | + | + | + | TNFα | + | − | n.a. | − | + |
| IL-18 | − | − | + | + | + | IL-18 | − | + | n.a. | − | + |
| IL-8 | + | − | − | − | − | IL-8 | + | − | n.a. | − | + |
| IL-10 | − | − | − | − | − | IL-10 | − | − | − | − | − |
| IL-2 | − | n.a. | n.a. | n.a. | n.a. | IL-2 | + | + | + | + | + |
| IL-1β | − | n.a. | n.a. | n.a. | n.a. | IL-1β | + | + | + | + | + |
| IL-5 | n.a. | n.a. | n.a. | n.a. | n.a. | IL-5 | + | + | + | + | + |

"n.a." = not analyzed;
"+" indicates an increase; and
"−" indicates no change relative to untreated cells (medium). The cytokine levels (pg/ml) were measure by ELISA 48 h after exposure to HMGB1-Bx or the particular HMGB1 peptide.

Of the 16 HMGB1 peptides that were tested, 3 peptides (i.e., Hp-31, Hp-91 and Hp-106) induced cytokine secretion in both human and murine DCs, while peptide Hp-16 stimulated cytokine secretion in murine, but not human DCs. These results indicate that peptides Hp-31, Hp-91, Hp-106 and Hp-16 could be used to produce antibodies having potential anti-inflammatory properties.

Example 2

Select HMGB1 Peptides Induce Phenotypic Maturation of Murine BM-DCs

Materials and Methods

In order to determine whether HMGB1-Bx and/or particular HMGB1 peptides could induce phenotypic maturation of murine DCs, immature BM-DCs were exposed to either HMGB1-Bx, a particular HMGB1 peptide, or LPS (FIG. 3). Fluorescence activated cell sorting (FACS) analysis was performed on immature DCs that were cultured in the presence of either HMGB1-Bx (50 µg/ml), an HMGB1 peptide (200 µg/ml), or LPS (100 ng/ml). Untreated DCs (medium) were also tested as a control. DCs were gated on $CD11c^+$ cells and analyzed for expression of specific maturation markers (e.g., CD86, MHC-II, CD40) by surface membrane immunofluorescence. In particular, $1 \times 10^4$ DCs were reacted for at least 20 min at 4° C. in 100 ml of PBS/5% FCS/0.1% sodium azide (staining buffer) with fluorescein isothiocyanate (FITC)-conjugated IgG monoclonal antibodies (mAbs) that are specific for CD86, CD40 or MHC-II (eBioscience). Cells were then washed 4 times with staining buffer, fixed in 10% formaldehyde in PBS (pH 7.2-7.4) and examined by flow cytometry using a FACScan (BD Biosciences). In all experiments, isotype controls were included using a FITC-conjugated irrelevant mAb of the same Ig class. Results are depicted as mean fluorescence intensity (MFI).

Results

Figure 3A:
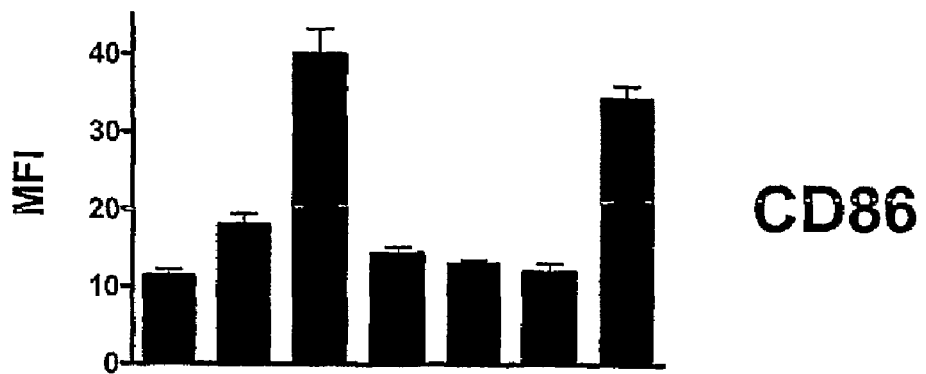
FIG. 3A is a bar graph depicting expression levels of CD86 on the surface of BM-DCs following exposure to the entire B-box domain (HMGB1-Bx), a particular HMGB1-derived peptide (Hp-16, Hp-46, Hp-106 or Hp-121), or LPS. Untreated cells (medium) are included as a control. One representative experiment of three experiments is depicted.
Figure 3B:
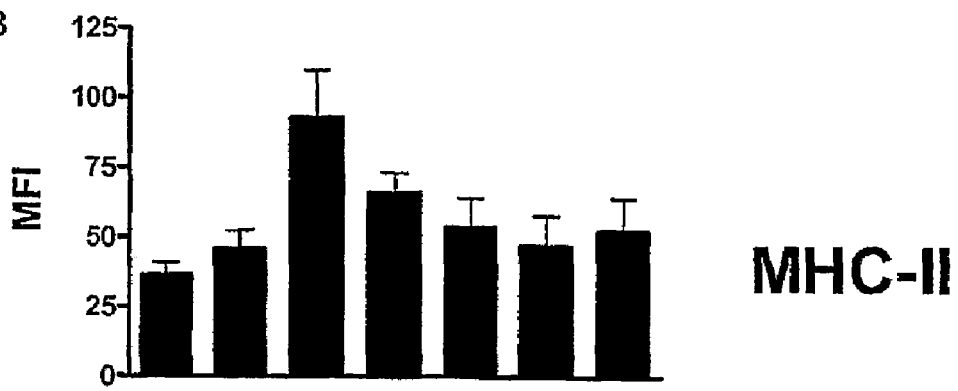
FIG. 3B is a bar graph depicting expression levels of MHC-II on the surface of BM-DCs following exposure to the entire B-box domain (HMGB1-Bx), a particular HMGB1-derived peptide (Hp-16, Hp-46, Hp-106 or Hp-121), or LPS. Untreated cells (medium) are included as a control. One representative experiment of three experiments is depicted.
Figure 3C:
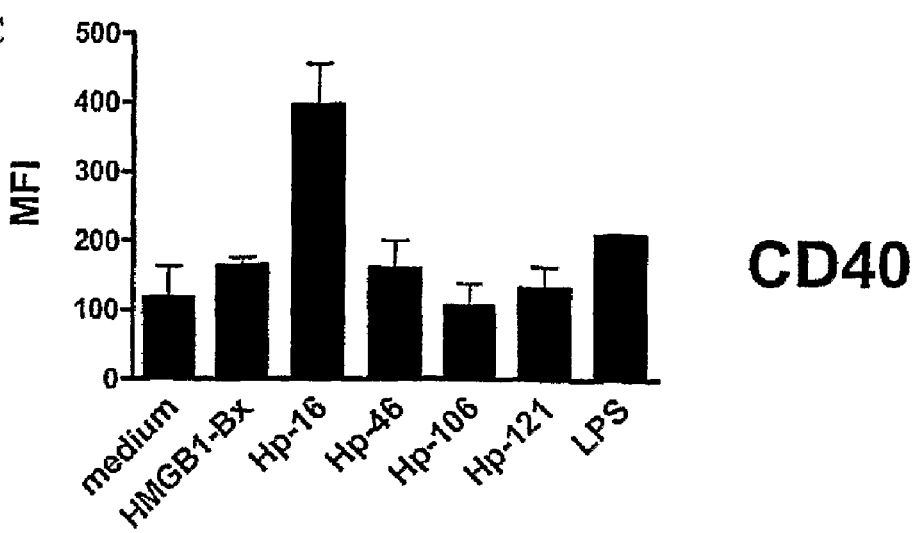
FIG. 3C is a bar graph depicting expression levels of CD40 on the surface of BM-DCs following exposure to the entire B-box domain (HMGB1-Bx), a particular HMGB1-derived peptide (Hp-16, Hp-46, Hp-106 or Hp-121), or LPS. Untreated cells (medium) are included as a control. One representative experiment of three experiments is depicted

HMGB1-Bx induced a small increase in CD86 expression (FIG. 3A) and had no effect on MHC-II or CD40 expression (FIGS. 3B and 3C) in BM-DCs. In contrast, the Hp-16 peptide induced a strong upregulation of CD86, MHC-II, and CD40 to levels that were comparable to, or higher than, those generated by LPS stimulation. Although Hp-106 induced high levels of cytokine secretion in BM-DCs, this peptide did not significantly enhance the surface expression of maturation markers. No altered expression in MHC-II, CD86, or CD40 was detected after exposing BM-DCs to the control peptide Hp-121 (FIG. 3A-3C).

Example 3

HMGB1-Bx and Select HMGB1 Peptides Induce Functional Maturation of BM-DCs

Materials and Methods

Figure 4A:
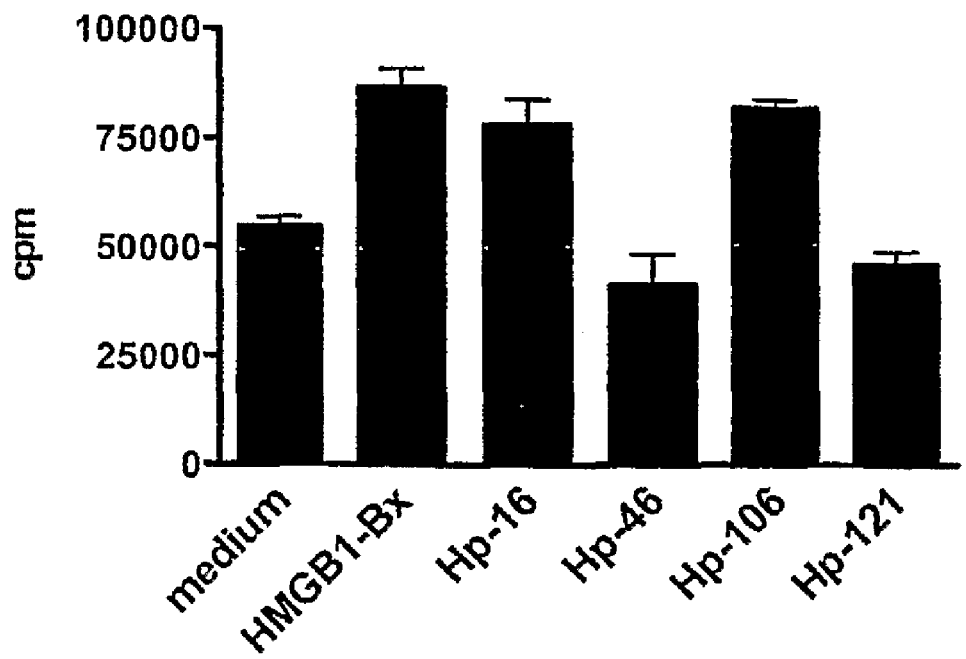
FIG. 4A is a bar graph depicting $^3$H thymidine incorporation in allogeneic T-cells that were co-cultured with DCs, which were isolated from C57/BL6 mice and had been exposed to either the entire B-box domain (HMGB1-Bx) or a particular HMGB1-derived peptide (Hp-16, Hp-46, Hp-106 or Hp-121). Responses are reported as mean counts per minute (cpm) of thymidine incorporation by triplicate cultures (+/− SEM). A representative example of three independent experiments is shown as mean cpm, +/− SEM, from triplicate cultures.

Immature BM-DCs that were generated from C57/BL6 mice (FIG. 4A) or Balb/c mice (FIG. 4B) were incubated for 48 h with either HMGB1-Bx (50 µg/ml), a particular HMGB1 peptide (200 µg/ml), LPS (100 ng/ml) or were left untreated (medium). T cells were isolated by negative selection using the mouse SpinSep antibody cocktail from StemCell Technologies (Vancouver, Calif.), according to the manufacturer's instructions. The cell purity of the isolated T cells was routinely ~99% pure. In order to assess levels of T cell activation and proliferation, cells were plated at $10^5$ cells per well in a round-bottomed 96-well tray at a DC:T cell ratio of 1:120 for 5 days in the medium described above. The microcultures were pulsed with ($^3$H)-thymidine (1 mCi/well) for the final 8 h of culture. Cell cultures were harvested onto glass fiber filters with an automated multiple sample harvester and the amount of isotope incorporation was determined by liquid scintillation β-emission. Responses are reported as mean cpm of thymidine incorporation by triplicate cultures (±SEM).

Results

Figure 4B:
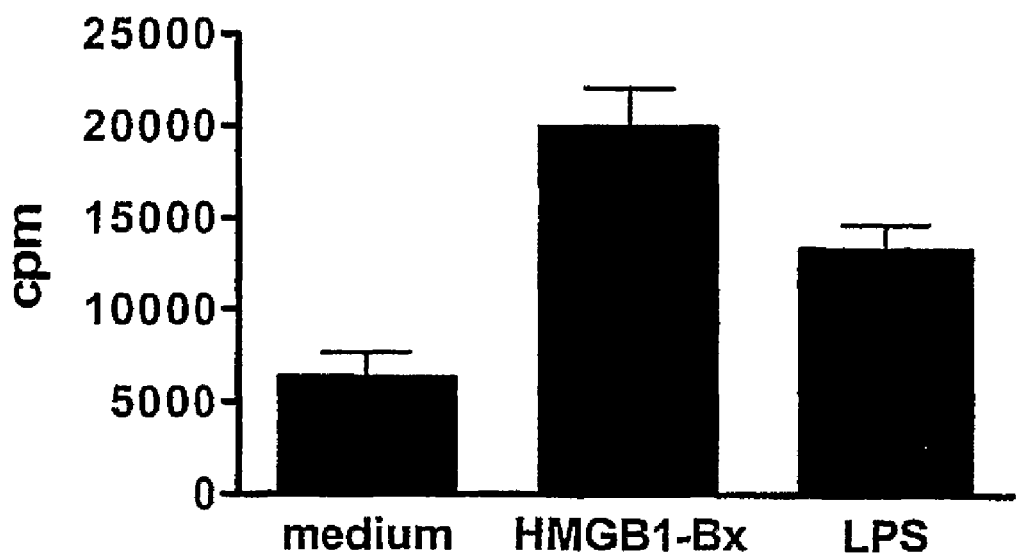
FIG. 4B is a bar graph depicting $^3$H thymidine incorporation in allogeneic T-cells that were co-cultured with DCs, which were isolated from Balb/c mice and had been exposed to either the entire B-box domain (HMGB1-Bx), LPS, or were untreated (medium). Responses are reported as mean counts per minute (cpm) of thymidine incorporation by triplicate cultures (+/− SEM). A representative example of three independent experiments is shown as mean cpm, +/− SEM, from triplicate cultures.

Mature, cytokine-producing DCs induce T cell activation and proliferation, leading to the development of adaptive immunity (Banchereau, J., and R. M. Steinman, *Nature* 392: 245-252 (1998); Rescigno, M., et al., *J. Leukoc. Biol.* 61:415-421(1997)). BM-DCs that were exposed to HMGB1-Bx, Hp-16 or Hp-106 activated proliferation of resting allogeneic T cells in a mixed lymphocyte reaction (FIG. 4A), whereas DCs exposed to Hp-46 or Hp-121 did not show enhanced T cell stimulatory activity. In order to investigate whether the functional maturation of DCs caused by exposure to HMGB1-Bx was strain specific, BM-DCs were generated from Balb/c mice. As observed with BM-DCs generated from C57/BL6 mice, HMGB1-Bx treated BM-DCs showed a strong capacity to induce T cell proliferation (FIG. 4B).

While this invention has been particularly shown and described with references to preferred embodiments thereof, it will be understood by those skilled in the art that various changes in form and details may be made therein without departing from the scope of the invention encompassed by the appended claims.

What is claimed is:

1. An antibody or antigen-binding fragment thereof that specifically binds to an HMGB1 polypeptide consisting of SEQ ID NO:6, wherein said antibody or antigen-binding fragment binds an epitope comprising the sequence Cys-Ser-Glu.

2. The antibody or antigen-binding fragment of claim 1, wherein said antibody or antigen-binding fragment inhibits release of a cytokine from a vertebrate cell treated with HMGB1.

3. The antibody or antigen-binding fragment of claim 2, wherein said cytokine is selected from the group consisting of IL-6, IL-12, TNF-α, IL-18, IL-8, IL-2, IL-1β and IL-5.

4. The antibody or antigen-binding fragment of claim 1, wherein said antibody or antigen-binding fragment is an antigen-binding fragment selected from the group consisting of an Fab fragment, an Fab' fragment, an F(ab')$_2$ fragment and an Fv fragment.

5. The antibody or antigen-binding fragment of claim 1, wherein said antibody or antigen-binding fragment is selected from the group consisting of a monoclonal antibody, a human antibody, a humanized antibody, a chimeric antibody, and an antigen-binding fragment of any of the foregoing.

6. An isolated cell that produces the antibody or antigen-binding fragment thereof of claim 1.

7. The isolated cell of claim 6, wherein said isolated cell is selected from the group consisting of an immortalized B cell, a hybridoma and a recombinant cell comprising one or more exogenous nucleic acid molecules that encode said antibody or antigen-binding fragment thereof.

8. The isolated cell of claim 6, wherein said antibody or antigen-binding fragment is a monoclonal antibody or an antigen-binding fragment thereof.

9. A composition comprising the antibody or antigen-binding fragment of claim 1 and a pharmaceutically-acceptable excipient.

10. A test kit for use in detecting the presence of an HMGB1 polypeptide or fragment thereof in a sample comprising:
  a) the antibody or antigen-binding fragment thereof of claim 1; and
  b) one or more ancillary reagents suitable for detecting the presence of a complex between said antibody or antigen-binding fragment and said HMGB1 polypeptide or fragment thereof.

11. A monoclonal antibody or antigen-binding fragment thereof that specifically binds to an HMGB1 polypeptide consisting of SEQ ID NO:6, or a fragment thereof, and wherein the antibody or antigen-binding fragment thereof inhibits release of TNF-α from a human dendritic cell treated with HMGB1, and further wherein the antibody or antigen-binding fragment thereof binds an epitope comprising the sequence Cys-Ser-Glu.

* * * * *

SEQUENCE LISTING

```
<160> NUMBER OF SEQ ID NOS: 19

<210> SEQ ID NO 1
<211> LENGTH: 215
<212> TYPE: PRT
<213> ORGANISM: Homo sapiens

<400> SEQUENCE: 1

Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
            20                  25                  30

Asp Ala Ser Val Asn Phe Ser Glu Phe Ser Lys Lys Cys Ser Glu Arg
        35                  40                  45

Trp Lys Thr Met Ser Ala Lys Glu Lys Gly Lys Phe Glu Asp Met Ala
    50                  55                  60
```

-continued

Lys Ala Asp Lys Ala Arg Tyr Glu Arg Glu Met Lys Thr Tyr Ile Pro
65                  70                  75                  80

Pro Lys Gly Glu Thr Lys Lys Phe Lys Asp Pro Asn Ala Pro Lys
            85                  90                  95

Arg Pro Pro Ser Ala Phe Phe Leu Phe Cys Ser Glu Tyr Arg Pro Lys
                100                 105                 110

Ile Lys Gly Glu His Pro Gly Leu Ser Ile Gly Asp Val Ala Lys Lys
            115                 120                 125

Leu Gly Glu Met Trp Asn Asn Thr Ala Ala Asp Lys Gln Pro Tyr
    130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp Ala Ala Lys Lys Gly Val Val
                165                 170                 175

Lys Ala Glu Lys Ser Lys Lys Lys Glu Glu Glu Asp Glu Glu
            180                 185                 190

Asp Glu Glu Asp Glu Glu Glu Glu Asp Glu Glu Asp Glu Asp Glu
            195                 200                 205

Glu Glu Asp Asp Asp Asp Glu
            210                 215

<210> SEQ ID NO 2
<211> LENGTH: 77
<212> TYPE: PRT
<213> ORGANISM: Homo sapiens

<400> SEQUENCE: 2

Pro Arg Gly Lys Met Ser Ser Tyr Ala Phe Phe Val Gln Thr Cys Arg
1               5                   10                  15

Glu Glu His Lys Lys Lys His Pro Asp Ala Ser Val Asn Phe Ser Glu
                20                  25                  30

Phe Ser Lys Lys Cys Ser Glu Arg Trp Lys Thr Met Ser Ala Lys Glu
            35                  40                  45

Lys Gly Lys Phe Glu Asp Met Ala Lys Ala Asp Lys Ala Arg Tyr Glu
    50                  55                  60

Arg Glu Met Lys Thr Tyr Ile Pro Pro Lys Gly Glu Thr
65                  70                  75

<210> SEQ ID NO 3
<211> LENGTH: 74
<212> TYPE: PRT
<213> ORGANISM: Homo sapiens

<400> SEQUENCE: 3

Phe Lys Asp Pro Asn Ala Pro Lys Arg Pro Pro Ser Ala Phe Phe Leu
1               5                   10                  15

Phe Cys Ser Glu Tyr Arg Pro Lys Ile Lys Gly Glu His Pro Gly Leu
                20                  25                  30

Ser Ile Gly Asp Val Ala Lys Lys Leu Gly Glu Met Trp Asn Asn Thr
            35                  40                  45

Ala Ala Asp Asp Lys Gln Pro Tyr Glu Lys Lys Ala Ala Lys Leu Lys
    50                  55                  60

Glu Lys Tyr Glu Lys Asp Ile Ala Ala Tyr
65                  70

<210> SEQ ID NO 4
<211> LENGTH: 18

```
<212> TYPE: PRT
<213> ORGANISM: Homo sapiens

<400> SEQUENCE: 4

Met Gly Lys Gly Asp Pro Lys Lys Pro Arg Gly Lys Met Ser Ser Tyr
1               5                   10                  15

Ala Phe

<210> SEQ ID NO 5
<211> LENGTH: 18
<212> TYPE: PRT
<213> ORGANISM: Homo sapiens

<400> SEQUENCE: 5

Tyr Ala Phe Phe Val Gln Thr Cys Arg Glu Glu His Lys Lys Lys His
1               5                   10                  15

Pro Asp

<210> SEQ ID NO 6
<211> LENGTH: 18
<212> TYPE: PRT
<213> ORGANISM: Homo sapiens

<400> SEQUENCE: 6

His Pro Asp Ala Ser Val Asn Phe Ser Glu Phe Ser Lys Lys Cys Ser
1               5                   10                  15

Glu Arg

<210> SEQ ID NO 7
<211> LENGTH: 18
<212> TYPE: PRT
<213> ORGANISM: Homo sapiens

<400> SEQUENCE: 7

Ser Glu Arg Trp Lys Thr Met Ser Ala Lys Glu Lys Gly Lys Phe Glu
1               5                   10                  15

Asp Met

<210> SEQ ID NO 8
<211> LENGTH: 18
<212> TYPE: PRT
<213> ORGANISM: Homo sapiens

<400> SEQUENCE: 8

Glu Asp Met Ala Lys Ala Asp Lys Ala Arg Tyr Glu Arg Glu Met Lys
1               5                   10                  15

Thr Tyr

<210> SEQ ID NO 9
<211> LENGTH: 18
<212> TYPE: PRT
<213> ORGANISM: Homo sapiens

<400> SEQUENCE: 9

Lys Thr Tyr Ile Pro Pro Lys Gly Glu Thr Lys Lys Phe Lys Asp
1               5                   10                  15

Pro Asn

<210> SEQ ID NO 10
<211> LENGTH: 18
<212> TYPE: PRT
<213> ORGANISM: Homo sapiens
```

-continued

```
<400> SEQUENCE: 10

Asp Pro Asn Ala Pro Lys Arg Pro Pro Ser Ala Phe Phe Leu Phe Cys
1               5                   10                  15
Ser Glu

<210> SEQ ID NO 11
<211> LENGTH: 18
<212> TYPE: PRT
<213> ORGANISM: Homo sapiens

<400> SEQUENCE: 11

Cys Ser Glu Tyr Arg Pro Lys Ile Lys Gly Glu His Pro Gly Leu Ser
1               5                   10                  15
Ile Gly

<210> SEQ ID NO 12
<211> LENGTH: 18
<212> TYPE: PRT
<213> ORGANISM: Homo sapiens

<400> SEQUENCE: 12

Ile Lys Gly Glu His Pro Gly Leu Ser Ile Gly Asp Val Ala Lys Lys
1               5                   10                  15
Leu Gly

<210> SEQ ID NO 13
<211> LENGTH: 18
<212> TYPE: PRT
<213> ORGANISM: Homo sapiens

<400> SEQUENCE: 13

Ser Ile Gly Asp Val Ala Lys Lys Leu Gly Glu Met Trp Asn Asn Thr
1               5                   10                  15
Ala Ala

<210> SEQ ID NO 14
<211> LENGTH: 18
<212> TYPE: PRT
<213> ORGANISM: Homo sapiens

<400> SEQUENCE: 14

Trp Asn Asn Thr Ala Ala Asp Asp Lys Gln Pro Tyr Glu Lys Lys Ala
1               5                   10                  15
Ala Lys

<210> SEQ ID NO 15
<211> LENGTH: 18
<212> TYPE: PRT
<213> ORGANISM: Homo sapiens

<400> SEQUENCE: 15

Thr Ala Ala Asp Asp Lys Gln Pro Tyr Glu Lys Lys Ala Ala Lys Leu
1               5                   10                  15
Lys Glu

<210> SEQ ID NO 16
<211> LENGTH: 18
<212> TYPE: PRT
<213> ORGANISM: Homo sapiens

<400> SEQUENCE: 16
```

```
Leu Lys Glu Lys Tyr Glu Lys Asp Ile Ala Ala Tyr Arg Ala Lys Gly
1               5                   10                  15

Lys Pro

<210> SEQ ID NO 17
<211> LENGTH: 18
<212> TYPE: PRT
<213> ORGANISM: Homo sapiens

<400> SEQUENCE: 17

Gly Lys Pro Asp Ala Ala Lys Lys Gly Val Val Lys Ala Glu Lys Ser
1               5                   10                  15

Lys Lys

<210> SEQ ID NO 18
<211> LENGTH: 18
<212> TYPE: PRT
<213> ORGANISM: Homo sapiens

<400> SEQUENCE: 18

Ser Lys Lys Lys Lys Glu Glu Glu Glu Asp Glu Glu Asp Glu Glu Asp
1               5                   10                  15

Glu Glu

<210> SEQ ID NO 19
<211> LENGTH: 20
<212> TYPE: PRT
<213> ORGANISM: Homo sapiens

<400> SEQUENCE: 19

Asp Glu Glu Glu Glu Asp Glu Glu Asp Glu Asp Glu Glu Glu Glu Asp
1               5                   10                  15

Asp Asp Asp Glu
            20
```